US012806210B2

(12) United States Patent
Dudley et al.

(10) Patent No.: US 12,806,210 B2
(45) Date of Patent: *Nov. 24, 2026

(54) METHODS OF TREATING TESTOSTERONE DEFICIENCY

(71) Applicant: Tolmar, Inc., Fort Collins, CO (US)

(72) Inventors: Robert E. Dudley, Murfreesboro, TN (US); Theodore Danoff, Philadelphia, PA (US); James A. Longstreth, Mundelein, IL (US)

(73) Assignee: Tolmar, Inc., Ft. Collins, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/433,069

(22) Filed: Feb. 5, 2024

(65) Prior Publication Data

US 2024/0180927 A1 Jun. 6, 2024

Related U.S. Application Data

(63) Continuation of application No. 18/451,557, filed on Aug. 17, 2023, which is a continuation of application No. 17/235,439, filed on Apr. 20, 2021, now abandoned, which is a continuation of application No. 16/720,194, filed on Dec. 19, 2019, now abandoned.

(60) Provisional application No. 62/782,865, filed on Dec. 20, 2018.

(51) Int. Cl.

| | |
|---|---|
| ***A61K 31/568*** | (2006.01) |
| ***A61K 9/00*** | (2006.01) |
| ***A61K 47/12*** | (2006.01) |
| ***A61K 47/44*** | (2017.01) |
| ***A61P 5/26*** | (2006.01) |

(52) U.S. Cl.
CPC .......... *A61K 31/568* (2013.01); *A61K 9/0053* (2013.01); *A61K 47/12* (2013.01); *A61K 47/44* (2013.01); *A61P 5/26* (2018.01)

(58) Field of Classification Search
CPC ........ A61K 31/568; A61K 9/0053; A61P 5/26
See application file for complete search history.

(56) References Cited

U.S. PATENT DOCUMENTS

| | | | |
|---|---|---|---|
| 3,164,520 | A | 1/1965 | Huber |
| 3,266,991 | A | 8/1966 | Wettstein |
| 4,147,783 | A | 4/1979 | van der Vies |
| 4,220,599 | A | 9/1980 | van der Vies |
| 4,572,915 | A | 2/1986 | Crooks |
| 4,719,239 | A | 1/1988 | Muller |
| 4,874,795 | A | 10/1989 | Yesair |
| 5,342,625 | A | 8/1994 | Hauer |
| 5,605,929 | A | 2/1997 | Liao |
| 5,645,856 | A | 7/1997 | Lacy |

(Continued)

FOREIGN PATENT DOCUMENTS

| | | |
|---|---|---|
| CN | 1686143 | 10/2005 |
| EP | 0904064 | 10/2001 |

(Continued)

OTHER PUBLICATIONS

2005 U.S. Pharmacopeia National Formulary, USP 28 NF 23, Official Jan. 1, 2005, 4 pages.

(Continued)

*Primary Examiner* — San Ming R Hui
(74) *Attorney, Agent, or Firm* — Ballard Spahr LLP

(57) ABSTRACT

Methods of treating a testosterone deficiency or its symptoms with a pharmaceutical formulation of testosterone undecanoate are provided.

23 Claims, 2 Drawing Sheets

(56) References Cited

U.S. PATENT DOCUMENTS 5,891,469 A 4/1999 Amselem
6,013,665 A 1/2000 Demichele
6,054,136 A 4/2000 Farah
6,096,338 A 8/2000 Lacy
6,140,375 A 10/2000 Nagahama
6,160,007 A 12/2000 Demichele
6,191,105 B1 2/2001 Ekwuribe
6,248,363 B1 6/2001 Patel
6,267,985 B1 7/2001 Chen
6,280,770 B1 8/2001 Path er
6,294,192 B1 9/2001 Patel
6,303,662 B1 10/2001 Nagahama
6,306,434 B1 10/2001 Hong
6,309,663 B1 10/2001 Patel
6,309,665 B2 10/2001 Barthelemy
6,312,704 B1 11/2001 Farah
6,383,471 B1 5/2002 Chen
6,451,339 B2 9/2002 Patel
6,458,383 B2 10/2002 Chen
6,569,463 B2 5/2003 Patel
6,623,765 B1 9/2003 Dennis
6,652,880 B1 11/2003 Aylwin
6,665,880 B2 12/2003 Poppe
6,761,903 B2 7/2004 Chen
6,923,988 B2 8/2005 Patel
6,982,281 B1 1/2006 Chen
7,025,979 B2 4/2006 Nieschlag
7,374,779 B2 5/2008 Chen
7,718,640 B2 5/2010 Hubler
8,241,664 B2 8/2012 Dudley
8,338,395 B2 12/2012 Hubler
8,367,103 B2 2/2013 Bardani
8,492,369 B2 7/2013 Dudley
8,771,233 B2 7/2014 Watanabe
8,778,916 B2 7/2014 Dudley
8,778,917 B2 7/2014 Dudley
8,778,922 B2 7/2014 Giliyar
8,828,428 B1 9/2014 Dudley
8,865,695 B2 10/2014 Giliyar
9,034,858 B2 5/2015 Giliyar
9,205,057 B2 12/2015 Giliyar
9,358,241 B2 6/2016 Giliyar
9,480,690 B2 11/2016 Giliyar
9,757,390 B2 9/2017 Giliyar
9,763,960 B2 9/2017 Krumme et al.
9,949,985 B2 4/2018 Giliyar
10,226,473 B2 3/2019 Giliyar
10,245,273 B2 4/2019 Dudley et al.
10,258,631 B2 4/2019 Josephs
10,543,219 B2 1/2020 Dudley
10,617,696 B2 4/2020 Dudley
11,179,402 B2 11/2021 Dudley
11,179,403 B2 11/2021 Dudley
11,331,325 B2 5/2022 Dudley et al.
11,426,416 B2 8/2022 Dudley et al.
11,564,933 B2 1/2023 Dudley et al.
2001/0018069 A1 8/2001 Johnson
2002/0012680 A1 1/2002 Patel
2002/0068693 A1 6/2002 Jeng et al.
2002/0103176 A1 8/2002 Nieschlag
2002/0106176 A1 8/2002 Kordahi et al.
2003/0022875 A1 1/2003 Wilson et al.
2003/0044434 A1 3/2003 Gao
2003/0072798 A1 4/2003 Schwarz
2003/0077297 A1 4/2003 Chen
2003/0104048 A1 6/2003 Patel
2003/0180352 A1 9/2003 Patel
2003/0181431 A1 9/2003 Hodgen et al.
2003/0186892 A1 10/2003 Taneja
2003/0235595 A1 12/2003 Chen
2003/0236236 A1 12/2003 Chen
2004/0002445 A1 1/2004 Taneja
2004/0053894 A1 3/2004 Mazess et al.
2004/0115287 A1 6/2004 Chen
2004/0127476 A1 7/2004 Kershman
2005/0032762 A1 2/2005 Hubler
2005/0096296 A1 5/2005 Fikstad
2005/0096365 A1 5/2005 Fikstad
2005/0100608 A1 5/2005 Ebert
2005/0101517 A1 5/2005 De Nijs
2005/0129718 A1 6/2005 Sherman
2005/0171193 A1 8/2005 Chen
2005/0176692 A1 8/2005 Amory
2005/0233970 A1 10/2005 Garnick
2005/0287203 A1 12/2005 Nijs De
2006/0003002 A1 1/2006 Fikstad
2006/0034937 A1 2/2006 Patel
2007/0232548 A1 10/2007 Taneja
2008/0020053 A1 1/2008 Persson
2008/0217692 A1 9/2008 Anderson
2008/0317844 A1 12/2008 Dudley
2008/0317850 A1 12/2008 Hewitt
2009/0074859 A1 3/2009 Patel
2010/0136105 A1 6/2010 Chen
2010/0137271 A1 6/2010 Chen
2010/0173882 A1 7/2010 Giliyar
2011/0039814 A1 2/2011 Huatan
2011/0142945 A1 6/2011 Chen
2011/0251167 A1 10/2011 Dudley
2012/0135069 A1 5/2012 Keck
2012/0135074 A1 5/2012 Giliyar
2012/0148675 A1 6/2012 Chickmath
2012/0244215 A1 9/2012 Giliyar
2012/0309731 A1 12/2012 Dudley
2012/0322780 A1 12/2012 Giliyar
2013/0022674 A1 1/2013 Dudley
2013/0045271 A1 2/2013 Dadey
2013/0052263 A1 2/2013 Fikstad
2013/0225544 A1 8/2013 Nachaegari
2013/0303495 A1 11/2013 Dhingra
2014/0011780 A1 1/2014 Dhingra
2014/0011789 A1 1/2014 Dudley
2014/0178466 A1 6/2014 Giliyar
2014/0249124 A1 9/2014 Dudley et al.
2014/0274986 A1 9/2014 Dudley
2014/0288039 A1 9/2014 Nachaegari
2014/0296199 A1 10/2014 Dudley
2014/0303129 A1 10/2014 Dudley
2014/0309202 A1 10/2014 Giliyar
2014/0357586 A1 12/2014 Patel
2015/0018324 A1 1/2015 Chickmath
2015/0038475 A1 2/2015 Chickmath
2015/0190406 A1 7/2015 Giliyar
2015/0273067 A1 10/2015 Patel
2015/0320765 A1 11/2015 Giliyar
2015/0343072 A1 12/2015 Dudley
2015/0343073 A1 12/2015 Dudley
2015/0343074 A1 12/2015 Dudley
2016/0000806 A1 1/2016 Dudley
2016/0184321 A1 6/2016 Patel
2016/0367569 A1 12/2016 Giliyar
2017/0007622 A1 1/2017 Giliyar
2017/0106002 A1 4/2017 Dudley et al.
2017/0119674 A1 5/2017 Bent
2017/0216312 A1 8/2017 Giliyar
2017/0246184 A1 8/2017 Dudley
2017/0246186 A1 8/2017 Giliyar
2017/0252357 A1 9/2017 Giliyar
2017/0348321 A1 12/2017 Krumme et al.
2018/0021350 A1 1/2018 Dudley
2018/0021351 A1 1/2018 Dudley
2018/0028542 A1 2/2018 Dudley
2018/0071311 A1 3/2018 Dudley et al.
2018/0078566 A1 3/2018 Dudley
2018/0110786 A1 4/2018 Dudley et al.
2018/0153905 A1 6/2018 Chidambaram
2018/0221387 A1 8/2018 Patel
2018/0243319 A1 8/2018 Dhingra
2018/0333423 A1 11/2018 Dudley et al.
2018/0353529 A1 12/2018 Kates
2019/0070196 A1 3/2019 Dudley
2019/0091239 A1 3/2019 Josephs
2019/0125760 A1 5/2019 Giliyar
2019/0175615 A1 6/2019 Nachaegari

(56) References Cited

U.S. PATENT DOCUMENTS

| | | | |
|---|---|---|---|
| 2019/0240235 | A1 | 8/2019 | Nachaegari |
| 2019/0240236 | A1 | 8/2019 | Chidambaram |
| 2019/0248830 | A1 | 8/2019 | Betageri |
| 2019/0298736 | A1 | 10/2019 | Josephs |
| 2019/0307772 | A1 | 10/2019 | Soni |
| 2019/0321374 | A1 | 10/2019 | Patel |
| 2020/0016172 | A1 | 1/2020 | Salameh et al. |
| 2020/0038411 | A1 | 2/2020 | Dudley |
| 2020/0046733 | A1 | 2/2020 | Dudley |
| 2020/0054648 | A1 | 2/2020 | Dudley |
| 2020/0093836 | A1 | 3/2020 | Dudley |
| 2020/0197412 | A1 | 6/2020 | Dudley et al. |
| 2020/0197413 | A1 | 6/2020 | Dudley et al. |
| 2021/0220374 | A1 | 7/2021 | Dudley |
| 2022/0088034 | A1 | 3/2022 | Dudley et al. |
| 2023/0105163 | A1 | 4/2023 | Dudley et al. |

FOREIGN PATENT DOCUMENTS

| | | |
|---|---|---|
| GB | 1264677 | 2/1972 |
| GB | 2228198 | 8/1990 |
| JP | H10503750 A | 4/1998 |
| JP | 2000 510458 | 8/2000 |
| JP | 2003 526620 | 10/2000 |
| JP | 2003 503440 | 1/2003 |
| JP | 2005 500347 | 1/2005 |
| KR | 20000065025 A | 11/2000 |
| WO | WO 1992/018147 | 10/1992 |
| WO | WO 1993/002664 | 2/1993 |
| WO | WO 1994/008610 | 4/1994 |
| WO | WO 1995/009512 | 4/1995 |
| WO | WO 1995/024893 | 9/1995 |
| WO | WO 1997/040823 | 11/1997 |
| WO | WO 1997/40823 | 11/1997 |
| WO | WO 1998/034621 | 8/1998 |
| WO | WO 2000/059482 | 10/2000 |
| WO | WO 2000/059512 | 10/2000 |
| WO | WO 2001/012155 | 2/2001 |
| WO | WO 2001/001960 | 11/2001 |
| WO | WO 2001/187316 | 11/2001 |
| WO | WO 2002/015938 | 2/2002 |
| WO | WO 2003/011300 | 2/2003 |
| WO | WO 2003/026649 | 4/2003 |
| WO | WO 2004/080383 | 9/2004 |
| WO | WO 2005/081742 | 9/2005 |
| WO | WO 2006/013369 | 2/2006 |
| WO | WO 2006/113505 | 10/2006 |
| WO | WO 2006/119498 | 11/2006 |
| WO | WO 2007/018943 | 2/2007 |
| WO | WO 2010/081032 | 7/2010 |
| WO | WO 2011/082384 | 7/2011 |
| WO | WO 2011/129812 | 10/2011 |
| WO | WO 2012/075081 | 6/2012 |
| WO | WO 2012/079092 | 6/2012 |
| WO | WO 2012/092202 | 7/2012 |
| WO | WO 2014/080282 | 5/2014 |
| WO | WO 2014/145518 | 9/2014 |
| WO | WO 2017/120592 | 7/2017 |
| WO | WO 2020/132163 | 6/2020 |

OTHER PUBLICATIONS

2015 U.S. Pharmacopeia National Formulary, USP 38 NF 33 through Second Supplement, Official Dec. 1, 2015 to Apr. 30, 2016 (12 pages).

Addo, S. et al., "Non-Polar Extracts of Serum from Males Contain Covert Radioimmunoassayable Testosterone," Steroids, 54(3):257-69, (1989).

Al-Sukhun, R. et al., "Lipid Drug Delivery Systems and Their Fate after Oral Administration," Ph.D. Dissertation, University of Bath, UMI No. U601432, ProQuest LLC: Ann Arbor, MI (2002).

Amory, J. et al., "Oral Testosterone in Oil Plus Dutasteride in Men: A Pharmacokinetic Study", J Clin Endocrinol Metab., 90(5):2610-7, (2005).

Anawalt, B. et al., "A Pharmacokinetic Study of Oral Testosterone Undecanoate (Org 538)", J Androl 37 Suppl., (2002).

Anby, M. et al., "Lipid Digestion as a Trigger for Supersaturation: Evaluation of the Impact of Supersaturation Stabilization on the in Vitro and in Vivo Performance of Self-Emulsifying Drug Delivery Systems," Mol Pharm., 9(7):2063-79, (2012).

Andriol® Testocaps® testosterone undecanoate (Consumer Medicine Information), AU registration No. AUST R 92904, NV Organon, (revised Sep. 2003).

Andriol® testosterone undecanoate capsules (Product Monograph), Control No. 181752, Merck Canada Inc., 26 pages, (revised: Jun. 2015).

Androderm® testosterone transdermal system (Product Label) Highlights of Prescribing Information, Distributed by Watson Pharma, Inc., 26 pages, (issued: Oct. 2011).

Androgel® testosterone gel (Product Label) Highlights of Prescribing Information, Reference ID: 2940032, Marketed by Abbott Laboratories, 14 pages, (revised: Apr. 2011).

Annonymous, "BCS, Its Significance and Application" as of Mar. 11, 2016.

Anonymous, "Lipocine Announces Positive Top-Line Results in Its Phase 3 Study of LPCN 1021 for Oral Testosterone Replacement Therapy", Lipocine Investor Room, retreived online at http://_irlipocine.com/Lipocine-Announces-Positive-Top-Line-Results-in-Its-Phase-3-Study-of-LPCN-10214 or-Oral-Testosterone-Replacement-Therapy, (2014).

Ansari, M. et al., "Microemulsions as Potential Drug Delivery Systems: A Review," PDAJ Pharm Sci Tech., 62(1):66-79, (2008).

Appendix 1—Glarus Exhibit List; Mar. 11, 2016.

Araya, H. et al., "The Novel Formulation Design of 0/W Microemulsion for Improving the Gastrointestinal Absorption of Poorly Water Soluble Compounds", Int J Pharm., 305(1-2):61-74, (2005).

Araya, H. et al., "The Novel Formulation Design of Self-emulsifying Drug Delivery Systems (SEDDS) Type 0/W Microemulsion I: Enhancing Effects on Oral Bioavailability of Poorly Water Soluble Compounds in Rats and Beagle Dogs", Drug Metab Pharmacokinet., 20(4):244-56, (2005).

Aveedt testosterone undecanoate (FDA Approval History), Drugs.com, 2 pages, (Mar. 8, 2016).

Aveedt testosterone undecanoate for Testosterone Replacement for Treatment of Hypogonadism, Briefing Document for Joint Meeting of Reproductive Health Drugs Advisory Committee & Drug Safety Risk Management Advisory Committee, Endo Pharmaceuticals Solutions, Inc., 145 pages, (Apr. 2013).

Avodarttm dutasteride Soft Gelatin Capsules (Prescribing Information), NDA 21-319/S-008, GlxoKlineSmith, 18 pages, (revised Aug. 2004).

BASF Technical Information entitled Cremophor Grades, Nonionic solubilizers and emulsifiers for the manufacture of cosmetic products, Oct. 2005.

BCS Classification—Formulations Report entitled Intra-Agency Agreement Between the Eunice Kennedy Shriver National Institute of Child Health and Human Development (NICHD) and the U.S. Food and Drug Administration (FDA) Oral Formulations Platform—Report 1 as of Mar. 11, 2016.

BCS Database Results for Alendronic Acid, Atorvastatin, Celecoxib, Fenofibrate, Glyburide (glibenclamide), Itraconazole, Lovastatin, Pioglitazone, Rofecoxib, Saquinavir, Simvastatin and Tacrolimus, as found on http://www.tsrlinc.net/search.cfm as of Mar. 11, 2016.

Bebb, R., "Testosterone deficiency: Practical guidelines for diagnosis and treatment, 2011", BC Med J., 53(9):474-9, (2011).

Bhasin, S. et al., "Testosterone Therapy in Men With Androgen Deficiency Syndromes: An Endocrine Society Clinical Practice Guideline", J Clin Endocrinol Metab., 95(6):2536-59, (2010).

Bhasin, S. et al., "Testosterone Therapy in Men With Hypogonadism: An Endocrine Society Clinical Practice Guideline", J Clin Endocrinol Metab., 103(5):1715-44, (2018).

Bittner, B. et al., "Formulations and Related Activities for the Oral Administration of Poorly Water-soluble Compounds in Early Discovery Animal Studies", Drugs made in Germany, 45(1):18-24, (2002).

(56) References Cited

OTHER PUBLICATIONS

Bittner, B. et al., "Formulations and Related Activities for the Oral Administration of Poorly Water-soluble Compounds in Early Discovery Animal Studies", Pharm Ind., 64(8):800-7, (2002).
Borage Seed Oil Certificate of Analysis; Manufacture Date: Apr. 2013; Retest Date: Apr. 2014; 1 page.
Bowtle, W. et al., "Materials, Process, and Manufacturing Considerations for Lipid-Based Hard-Capsule Formats", Chapter 4, pp. 79-106, in Oral Lipid Based Formulations; Enhancing the Bioavailability of Poorly Water-Soluble Drugs, Hauss, ed., Informa Healthcare USA, Inc.: New York, NY, (2007).
Brouwers, J. et al., "Supersaturating Drug Delivery Systems: The Answer to Solubility-Limited Oral Bioavailability?", J Pharm Sci., 98(8):2549-72, (2009).
Burbello, A. et al., "Sovremennye lekarstvennyesredstva S—Pb Neva", p. 567. (partial translation only), (2004).
Cantrill, J. et al., Which Testosterone Replacement Therapy?, Clin Endocrinol., 21(2):97-107, (1984).
Chakraborty, S. et al., "Lipid: An Emerging Platform for Oral Delivery of Drugs with Poor Bioavailability", Eur J Pharm Biopharm., 73(1):1-15, (2009).
Chambin, O. et al., "Interest of Multifunctional Lipid Excipients: Case of Gelucire 44/14", Drug Dev Ind Pharm., 31(6):527-34, (2005).
Chang, R., Ch. 12: Physical Properties of Solutions, Chemistry (8th Ed.), 5 pages, (2005).
Charman, S. et al., "Effects of Lipid Class and Lipid Vehicle vol. on the Intestinal Lymphatic Transport of DDT", Int J Pharm., 33(1-2):165-72, (1986).
Charman, S. et al., "Self-Emulsifying Drug Delivery Systems: Formulation and Biopharmaceutic Evaluation of an Investigational Lipophilic Compound", Pharm Res., 9(1):87-93, (1992).
Charman, W. et al., "Absorption of Danazol After Administration to Different Sites of the Gastrointestinal Tract and the Relationship to Single- and Double-Peak Phenomena in the Plasma Profiles", J Clin Pharmacol., 33(12):1207-13, (1993).
Charman, W. et al., "Effect of Food and a Monoglyceride Emulsion Formulation on Danazol Bioavailability", J Clin Pharmacol., 33(4):381-6, (1993).
Charman, W. et al., "Physicochemical and Physiological Mechanisms for the Effects of Food on Drug Absorption: The Role of Lipids and pH", J Pharm Sci., 86(3):269-82, (1997).
Charman, W., "Lipids, Lipophilic Drugs, and Oral Drug Delivery—Some Emerging Concepts", J Pharm Sci., 89(8):967-78, (2000).
Cheema, M. et al., "Lipid Vehicles for Intestinal Lymphatic Drug Absorption", J Pharm Pharmacol., 39(1):55-6, (1987).
Christensen, J. et al., "Solubilisation of Poorly Water-Soluble Drugs During In Vitro Lipolysis of Medium- and Long-Chain Triacylglycerols", Eur J Pharm Sci., 23(3):287-96, (2004).
Clarus Claim Chart as of Mar. 11, 2016 (33 pages).
Clarus Motion 1, to deny Lipocine benefit, Mar. 11, 2016.
Clarus Motions 2 and 3, to accord benefit, Mar. 11, 2016.
Glarus Therapeutics Press Release, "Clarus Therapeutics Receives U.S. FDA Approval of Jatenzo® (Testosterone Undecanoate Capsules for Oral Use) (CIII) for Testosterone Replacement Therapy in Certain Adult Men"; Aug. 13, 2020; 2 pages.
Glarus Therapeutics Press Release, "Glarus Therapeutics Receives U.S. FDA Approval of Jatenzo® (Testosterone Undecanoate Capsules for Oral Use) (CIII) for Testosterone Replacement Therapy in Certain Adult Men"; Mar. 27, 2019; 4 pages.
Clarus, ClinicalTrials.Gov Submission for CLAR-09007; NCT01403116 ; published online on Jul. 25, 2011.
Coert, A. et al., "The Pharmacology and Metabolism of Testosterone Undecanoate (TU), A New Orally Active Androgen", Acta Endocrinol (Copenh)., 79(4):789-800, (1975).
Complaint, *Clarus Therapeutics, Inc.* v- *Lipocine Inc., et al.* U.S. District Court for the District of Delaware. Civ. Action No. 1:15-cv-01004-RGA (Nov. 2, 2015); Exhibit A U.S. Pat. No. 8,828,428 issued Sep. 9, 2014.
Constantinides, et al., "Lipid Formulation Strategies for Enhancing Intestinal Transport and Absorption of P-Glycoprotein (P-gp) Substrate Drugs: In vitro/In vivo Case Studies," J. Pharm. Sci., 96: 235-48 (2007).
Constantinides, et al., "Tocol emulsions for drug solubilization and parenteral delivery," Adv. Drug Del. Rev., 56: 1243-55 (2004).
Constantinides, P. et al., "Advances in Lipid Nanodispersions for Parenteral Drug Delivery and Targeting", Adv Drug Del Rev., 60(6):757-67, (2008).
Constantinides, P. et al., "Advances in Lipid-Based Drug Solubilization and Targeting", Adv Drug Del Rev., 56(9):1239-40, (2004).
Constantinides, P. et al., "Advances in the Use of Tocols as Drug Delivery Vehicles", Pharm Res., 23(2):243-55, (2006).
Constantinides, P. et al., "Considerations and Recommendations on Traditional and Non-Traditional Uses of Excipients in Oral Drug Products", AAPS Open, 2:3, 1-6, (2016).
Constantinides, P. et al., "Formulation and Intestinal Absorption Enhancement Evaluation of Water-in-Oil Microemulsions Incorporating Medium-Chain Glycerides", Pharm Res., 11(10):1385-90, (1994).
Constantinides, P. et al., "Formulation and Physical Characterization of Water-in-Oil Microemulsions Containing Long Versus Medium-Chain Glycerides", Int J Pharm., 158(1):57-68, (1997).
Constantinides, P. et al., "Formulation Development and Antitumor Activity of a Filter-Sterilizable Emulsion of Paclitaxel", Pharm Res., 17(2):175-82, (2000).
Constantinides, P., "Lipid Microemulsions for Improving Drug Dissolution and Oral Absorption: Physical and Biopharmaceutical Aspects", Pharm Res., 12(11):1561-72, (1995).
Constantinides, P., "Self-Emulsifying Drug Delivery Formulations in the 21st Century: Challenges and Opportunities", Controlled Drug Delivery, ACS Symposium Series 752, Ch. 28, pp. 284-296, (2000).
Conway, A. et al., "Randomized Clinical Trial of Testosterone Replacement Therapy in Hypogonadal Men", Int J Androl., 11(4):247-64, (1988).
Corona, G. et al., "Update in Testosterone Therapy for Men", J Sex Med., 8(3):639-54, (2011).
Croda's Report on Myrj entitled Alkoxylated Fatty Acids (2009).
Cruine, J. et al., "Evaluation of the Impact of Surfactant Digestion on the Bioavailability of Danazol after Oral Administration of Lipidic Self-Emulsifying Formulations to Dogs", J Pharm Sci., 97(2):995-1012, (2008).
Cruine, J. et al., "Increasing the Proportional Content of Surfactant (Cremophor EL) Relative to Lipid in Self-emulsifying Lipid-based Formulations of Danazol Reduces Oral Bioavailability in Beagle Dogs", Pharm Res., 24(4):748-57, (2007).
Curriculum Vitae of Joel Frank as of Mar. 11, 2016; 1 page.
Curriculum Vitae of Mansoor M. Amiji, Ph.D., R.Ph., last updated Mar. 10, 2014.
Daggett, P. et al., "Oral Testosterone, a Reappraisal", Horm Res., 9(3):121-9, (1978).
Dahan, A. et al., "Enhanced Gastrointestinal Absorption of Lipophilic Drugs", Enhanc Drug Deliv., Ch. 6, pp. 111-131, (2006).
Dahan, A. et al., "Rationalizing the Selection of Oral Lipid Based Drug Delivery Systems by an In Vitro Dynamic Lipolysis Model for Improved Oral Bioavailability of Poorly Water Soluble Drugs", J Cont Rel., 129(1):1-10, (2008).
Dawson, B. et al., "Basic and Clinical Biostatistics", Third Edition, Chapter 4, (2001).
De La Torre, X. et al., "Detection of Testosterone Esters in Human Plasma", J Mass Spectrom., 30(10):1393-404, (1995).
Declaration of Edmund J. Elder, Jr., Ph.D., Mar. 11, 2016.
Declaration of Joel Frank, Mar. 11, 2016 (5 pages).
Declaration of Mansoor M. Amiji, Ph.D., R.Ph., Mar. 11, 2016.
Devani, M. et al., "The Emulsification and Solubilisation Properties of Polyglycolysed Oils in Self-Emulsifying Formulations", J Pharm Pharmacol., 56(3):307-17, (2004).
Dressman, J. et al., "Dissolution Testing as a Prognostic Tool for Oral Drug Absorption: Immediate Release Dosage Forms", Pharm Res., 15(1):11-22, (1998).

(56) References Cited

OTHER PUBLICATIONS

Dressman, J. et al., "In Vitro-In Vivo Correlations for Lipophilic, Poorly Water-Soluble Drugs", Eur J Pharm Sci., 11(Suppl 2):S73-80, (2000).
EP Application No. 10714521.1; Decision to Grant, dated Mar. 20, 2014; 52 pages.
EP Patent Application No. 10714521.1; Response to Examination Report, dated Jan. 30, 2014; pp. 6.
EP Patent Application No. 15186752.0; Excerpt from European Search Opinion, dated Apr. 11, 2015; 4 pages.
Erlich, L. et al., "Relative Bioavailability of Danazol in Dogs from Liquid-Filled Hard Gelatin Capsule", Int J Pharm., 179(1):49-53, (1999).
Excerpt from GlaxoSmithKline's New Drug Application No. 21-319 for Duagen (Dutasteride): Summary Review of Pharmacokinetics and Bioavailability, pp. 13-19 (Oct. 5, 2001).
Folia, C., "Testosterone Deficiency in Aging Men and its Treatment: Your Questions Answered", Free CE Lesson, 8 pages, (2007).
Fortestatm testosterone (Product Label) Highlights of Prescribing Information, Reference ID: 3371066, manufactured for Endo Pharmaceuticals Inc., 23 pages, (revised: Sep. 2013).
Gao, P. et al., "Design and Development of Supersaturatable Self-Emulsifying Drug Delivery Systems for Enhancing the Gastrointestinal Absorption of Poorly Soluble Drugs", Drugs and Pharm., 170(1):303-28, (2007).
Gao, P. et al., "Development of a Supersaturable SEDDS (S-SEDDS) Formulation of Paclitaxel with Improved Oral Bioavailability", J Pharm Sci., 92(12):2386-98, (2003).
Gao, P. et al., "Development of Supersaturatable Selfemulsifying Drug Delivery System Formulations for Improving the Oral Absorption of Poorly Soluble Drugs", Expert Opin Drug Deliv., 3(1):97-110, (2006).
Gershanik, T. et al., "Self-Dispersing Lipid Formulations for Improving Oral Absorption of Lipophilic Drugs", Eur J Pharm Biopharm., 50(1):179-88, (2000).
Gershkovich, P. et al., "Inhibition of Intestinal Absorption of Cholesterol by Surface-Modified Nanostructured Aluminosilicate Compounds", J Pharm Sci., 98(7):2390-400, (2009).
Ghafourian, T. et al., "Estimation of Drug Solubility in Water, PEG 400 and Their Binary Mixtures Using the Molecular Structures of Solutes", Eur J Pharm Sci., 40(5):430-40, (2010).
Ghosh, P. et al., "Design and Development of Microemulsion Drug Delivery System of Acyclovir for Improvement of Oral Bioavailability", AAPS PharmSciTech., 7(3):77, (2006).
Gibson, L., "Lipid-Based Excipients for Oral Drug Delivery", Oral Lipid-Based Formulations, 170:33-62, (2007).
Glaxosmithkline, "An Evaluation of the Relative Bioavailability of the GI 198745 (Dutasteride) Soft Gelatin Capsule with Monodiglycerides of Caprylic/Capric Acid (MDC) in Healthy Adult Male Volunteers," Clinical Study Register for Study No. ARIA1004, pp. 1-4, downloaded from http://_www.gskclinicalstudyregister.com/files2/917.pdf1109 (Jan. 2005).
Gooren, L. et al., "Androgen Replacement Therapy: Present and Future", Drugs, 64(17):1861-91, (2004).
Gould, D. et al., "Testosterone Replacement Therapy for Late Onset Hypogonadism: What Is the Risk of Inducing Prostate Cancer?", Prostate Cancer Prostatic Dis., 9(1):14-8, (2006).
Graham-Smith, D. et al., "The Oxford Reference-Book on Clinical Pharmacology and Pharmacotherapy", M. Meditsina Publishers, 5105, 4 pages, (2000).
Grove, M. et al., "Bioavailability of Seocalcitol II: Development and Characterisation of Self-Microemulsifying Drug Delivery Systems (SMEDDS) for Oral Administration Containing Mediumand Long Chain Triglycerides", Eur J Pharm Sci., 28(3):233-42, (2006).
Groves, M. et al., "The Self-Emulsifying Action of Mixed Surfactants in Oil", Acta Pharm Suec, 13(4):361-72, (1976).
Guleria, R. et al., "Polyethylene Glycol enhances solubility of Domperidone through Solid dispersion", Am J PharmTech Res., 2(2):630-8, (2012).
Gursoy, R. et al., "Self-Emulsifying Drug Delivery Systems (SEDDS) for Improved Oral Delivery of Lipophilic Drugs", Biomed Pharmacother., 58(3):173-82, (2004).
Handbook of Pharmaceutical Excipients, pp. 290-294, 6th Ed., (2009).
Handbook of Pharmaceutical Excipients, pp. 308-312 and 545-50, 5th Ed., (2006).
Haskell, R. et al., "Perspectives in Pharmaceutical Nanotechnology," AAPS Newsmagazine, pp. 16-23, (2012).
Hauss, D. et al., "Lipid-Based Delivery Systems for Improving the Bioavailability and Lymphatic Transport of a Poorly Water-Soluble LTB4 Inhibitor", J Pharm Sci., 87(2):164-9, (1998).
Hengge, U. et al., "Double-Blind, Randomized, Placebo-Controlled Phase III Trial of Oxymetholone for the Treatment of HIV wasting", AIDS, 17(5):699-710, (2003).
Hong, J. et al., "A New Self-Emulsifying Formulation of Itroconazole with Improved Dissolution and Oral Absorption", J Control Release, 110(2):332-8, (2006).
Houwing, N. et al., "Pharmacokinetic Study in Women of Three Different Doses of a New Formulation of Oral Testosterone Undecanoate, Andriol Testocaps", Pharmacotherapy, 23(10):1257-65, (2003).
Humberstone, A. et al., "Lipid-Based Vehicles for the Oral Delivery of Poorly Water Soluble Drugs", Adv Drug Deliv Rev., 25(1):103-28, (1997).
International Application No. PCT/US2006/014207; International Preliminary Report on Patentability, date of issuance Dec. 17, 2007; 4 pages.
International Application No. PCT/US2006/014207; International Search Report and Written Opinion of the International Searching Authority, date of mailing Nov. 28, 2007; 6 pages.
International Application No. PCT/US2010/030788; International Preliminary Report on Patentability, date of issuance Oct. 16, 2012; 5 pages.
International Application No. PCT/US2010/030788; International Search Report and Written Opinion of the International Searching Authority, date of mailing Dec. 1, 2010, 12 pages.
International Application No. PCT/US2014/030308; International Preliminary Report on Patentability, date of issuance Sep. 15, 2015; 4 pages.
International Application No. PCT/US2014/030308; Written Opinion of the International Searching Authority, date of mailing Aug. 5, 2014; 3 pages.
International Application No. PCT/US2018/033497; International Preliminary Report on Patentability, date of issuance Sep. 28, 2018; 7 pages.
International Application No. PCT/US2018/033497; International Search Report and Written Opinion of the International Searching Authority, date of mailing Aug. 9, 2018; 9 pages.
International Application No. PCT/US2019/067326; International Search Report and Written Opinion of the International Searching Authority, date of mailing Apr. 14, 2020; 13 pages.
IsoChem Technical Report entitled Vitamin E TPGS NF and Food Grade, Jun. 2012.
Jain, N. et al., "Estimation of the Aqueous Solubility 1: Application to Organic Nonelectrolytes", J Pharm Sci., 90(2):234-52, (2001).
James, K. et al., "Solubilities of Testosterone Proprionate and Related Esters in Organic Solvents", J Pharm Sci., 65(5):656-9, (1976).
James, K. et al., "The Solubilities of the Lower Testosterone Esters", J Pharm Pharmacol., 20(9):709-14, (1968).
Jannin, V. et al., "Approaches for the Development of Solid and Semi-Solid Lipid Based Formulations", Adv Drug Deliv Rev., 60(6):734-74, (2008).
Jatenzo® Prescribing Information; Revised Mar. 2019; 18 pages.
Jouyban, A., "Solubility Prediction of Drugs in Water-Polyethylene Glycol 400 Mixtures Using Jouyban-Acree model", Chem Pharm Bull (Tokyo), 54(11):1561-6, (2006).
Julianto, T. et al., "Improved Bioavailability of Vitamin E with a Self-Emulsifying Formulation", Int J Pharm., 200(25):53-7, (2000).
Jungwirth, A. et al., "Clinical Experience with Andrioll Testocaps1—The first Austrian Surveillance Study on the Treatment of Late-Onset Hypogonadism", The Aging Male, 10(4):183-7, (2007).

(56) References Cited

OTHER PUBLICATIONS

Kadajji, V. et al., "Water Soluble Polymers for Pharmaceutical Applications", Polymers, 3(4):1972-2009, (2011).
Kalinchenko, S., "Testosteron-Korol" J Sex Life, pp. 12-22 / online [retrieved on Mar. 26, 2010 13:27]. Retrieved from the Internet: URL:http://www.lazmed.ru/interesting/publications/ testosteron.html. (partial translation only), (2004).
Kang, B. et al., "Development of Self-Microemulsifying Drug Delivery Systems (SMEDDS) for Oral Bioavailability Enhancement of Simvastatin in Beagle Dogs", Int J Pharm., 274(1-2):65-73, (2004).
Kaukonen, A. et al., "Drug Solubilization Behavior During in Vitro Digestion of Simple Triglyceride Lipid Solution Formulaions", Pharm Res., 2(2):245-53, (2004).
Kaukonen, A. et al., "Drug Solubilization Behavior During in Vitro Digestion of Suspension Formulations of Poorly Water-Soluble Drugs in Triglyceride Lipids", Pharm Res., 21(2):254-60, (2004).
Kaur, N. et al., "Nanomedicine: Trends and Perspectives on Technologies and Products", Adv NanoTech Appls, 2(7):95-107, (2010).
Kawakami, K. et al., "Micro Emulsion Formulation for Enhanced Absorption of Poorly Soluble Drug I Prescription Design", J Controlled Rel., 81(1-2):65-74, (2002).
Khoo, S. et al., Formulation Design and Bioavailability Assessment of Lipidic Self-Emulsifying Formulations of Halofantrine, Int J Pharm., 167(1-2):155-64, (1998).
Kim, H. et al., "Preparation and In Vitro Evaluation of Self-Microemulsifying Drug Delivery Systems Containing Idebenone", Drug Dev Ind Pharm., 26(5):523-9, (2000).
Kincl, F. et al., "Increasing Intestinal Absorption of Drugs by Formulation", Arch Pharm (Weinheim), 319(7):615-24, (1986).
Kohn, F. et al., "A New Oral Testosterone Undecanoate Formulation", World J Urol., 21(5):311-5, (2003).
Kommuru, T. et al., "Self-Emulsifying Drug Delivery Systems (SEDDS) of Coenzyme Q10: Formulation Development and Bioavailability Assessment", Int J Pharm., 212(2):233-46, (2001).
Kossena, G. et al., "Probing Drug Solubilization Patterns in the Gastrointestinal Tract After Administration of Lipid-Based Delivery Systems: A Phase Diagram Approach", J Pharm Sci., 93(2):332-48, (2004).
Kossena, G. et al., "Separation and Characterization of the Colloidal Phases Produced on Digestion of Common Formulation Lipids and Assessment of their Impact on the Apparent Solubility of Selected Poorly Water-Soluble Drugs", J Pharm Sci., 92(3):634-48, (2003).
Kostewicz, E. et al., "Predicting the Precipitation of Poorly Soluble Weak Bases Upon Entry in the Small Intestine", J Pharm Pharmacol., 56(1):43-51, (2004).
Kuehl, P. et al., "Formulation and In Vivo Evaluation of Chlorpropham (CIPC) Oral Formulations", J Pharm Sci., 97(12):5222-8, (2008).
Lachance, S. et al., "Importance of Measuring Testosterone in Enzyme-Inhibited Plasma for Oral Testosterone Undecanoate Androgen Replacement Therapy Clinical Trials", Fut Sci., 1(4):1-10, (2015).
Lee, J., "Management of Androgen Decline in Aging Men", Geriatrics & Aging, 6(1):23-6, (2003).
Liang, T. et al., "Inhibition of Steriod 5a-Reductase by Specific Aliphatic Unsaturated Fatty Acids", Biochem J., 285(Pt2):557-62, (1992).
Lipocine Claim Chart with Fig. 5 and 9 as of Mar. 11, 2016 (11 pages).
*Lipocine Inc.* v. *Clarus Therapeutics, Inc.*, C.A. No. 19-622 (WCB); Memorandum Opinion and Order; Jun. 1, 2021; 67 pages.
Lipocine Inc.'s List of Exhibits; Mar. 11, 2016.
Lipocine Lab Notebook, pages showing PEG400/TU Solubility Experiment, as of Mar. 11, 2016 (2 pages).
Lipocine Motion 1, to accord benefit, Mar. 11, 2016.
Lipocine Motion 2, Enablement, Mar. 11, 2016.
Lipocine Press Release, "Lipocine Receives Complete Response Letter for Tlandotm from U.S. FDA"; Nov. 11, 2019; 2 pages.
Liu, C. et al., "Research and Development in Drug Innovation: Reflections from the 2013 Bioeconomy Conference in China, Lessons Learned and Future Perspectives", Acta Pharm Sin B., 4(2):112-9, (2014).
Loper, A. et al., "Equivalence of a Self-Emulsifying Drug Delivery System (SEDDS) and Soybean Oil for Oral Delivery of a 5a-Reductase Inhibitor in Rhesus Monkeys", Proc Eur Symp, pp. 369-372, (1996).
MacGregor, K. et al., "Lipolysis of Oily Formulations in the Gastro-Intestinal Tract", Adv Drug Deliv Rev., 25:33-46, (1997).
MacKenzie, G. et al., "Targeting Mitochondrial STAT3 with the Novel Phospho-Valproic Acid (MDC-1112) Inhibits Pancreatic Cancer Growth in Mice", PLoS One, 8(5):e61532, (2013).
Maisey, N. et al., "Clinical Efficacy of Testosterone Undecanoate in Male Hypogonadism", Clin Endocrinol (Oxf)., 14(6):625-9, (1981).
Maisine 35-1 Certificate of Analysis; Printed Feb. 23, 2012; 1 page.
Maisine 35-1 Technical Data Sheet; Nov. 9, 2011; 1 page.
Mattheolabakis, G. et al., "Nanodelivery Strategies in Cancer Chemotherapy: Biological Rationale and Pharmaceutical Perspectives", Nanomedicine (Lond)., 7(10):1577-90, (2012).
Mattheolabakis, G. et al., "Pegylation Improves the Pharmacokinetics and Bioavailability of Small-Molecule Drugs Hydrolyzable by Esterases: A Study of Phospho-Ibuprofen", J Pharmacol Exp Ther., 351(1):61-6, (2014).
Mattheolabakis, G. et al., "Sterically Stabilized Liposomes Incorporating the Novel Anticancer Agent Phospho-Ibuprofen (MDC-917): Preparation, Characterization, and In Vitro/In Vivo Evaluation", Pharm Res., 29(6):1435-43, (2012).
Miescher, K. et al., "CCLXXVII. The Activation of the Male Sex Hormones II.", Biochem J., pp. 1977-1990, (1936).
Miller, D. et al., "Targeted Intestinal Delivery of Supersaturated Itraconazole for Improved Oral Absorption", Pharm Res., 25(6):1450-9, (2008).
Mohsin, K. et al., Design of Lipid-Based Formulations for Oral Administration of Poorly Water-Soluble Drugs: Precipitation of Drug after Dispersion of Formulations in Aqueous Solution, J Pharm Sci., 98(10):3582-95, (2008).
Mooradian, A. et al., "A New Series of Testosterone Esters", 71(10):3372-4, (1949).
Morrison, R. et al., "Functional Derivatives of Carboxylic Acids", Org Chem., 20(18):680-1, (1976).
Muchow, M. et al., "Production and Characterization of Testosterone Undecanoate-Loaded NLC for Oral Bioavailability Enhancement", Drug Dev Ind Pharm., 37(1):8-14, (2011).
Muchow, M. et al., "Testosterone Undecanoate—Increase of Oral Bioavailability by Nanostructured Lipid Carriers (NLC)", J Pharm Tech Drug Res., pp. 1-10, (2013).
Mullertz, A. et al., "New Perspectives on Lipid and Surfactant Based Drug Delivery Systems for Oral Delivery of Poorly Soluble Drugs", J Pharm Pharmacol., 62(11):1622-36, (2010).
Nicolaides, E. et al., "Biorelevant Dissolution Testing to Predict the Plasma Profile of Lipophilic Drugs After Oral Administration", Pharm Res., 18(3):380-8, (2001).
Nieschlag, E. et al., "Testosterone Replacement Therapy: Current Trends and Future Directions", Hum Reprod Update, 10(5):409-19, (2004).
Noguchi, T. et al., "The Effect of Drug Lipophilicity and Lipid Vehicles on the Lymphatic Absorption of Various Testosterone", Int J Pharm., 24(2-3):173-84, (1985).
O'Driscoll, C., "Lipid-Based Formulations for Intestinal Lymphatic Delivery", Eur J Pharm Sci., 15(5):405-15, (2002).
Patel, J. et al., "Self-Emulsifying Delivery Systems for Poorly Absorbed Drugs", Int J Pharm Sci Nanotechnol., 1(2):123-8, (2008).
Patel, M. et al., "A Self Micro Emulsifying Drug Delivery System (SMEDDS)", Int J Pharm Sci Rev Res., 4(3):29-35, (2010).
Patent Interference No. 106,045 (McK); Paper 1; Declaration of Interference; Dec. 4, 2015.
Patent Interference No. 106,045 (McK); Paper 2; Standing Order; Dec. 4, 2015.
Patent Interference No. 106,045 (McK); Paper 3; Order—Motion Times; Dec. 4, 2015.
Patent Interference No. 106,045 (McK); Paper 4; Miscellaneous Order; Dec. 4, 2015.

(56) References Cited

OTHER PUBLICATIONS

Patent Interference No. 106,045; Decision on Motions; Sep. 20, 2017; 33 pages.
Patent Interference No. 106,045; Judgement, Entered Dec. 21, 2018; Submitted on Mar. 26, 2019; 3 pages.
Patent Interference No. 106,120 (DK); Paper 1; Decision on Motions; Nov. 16, 2020; 304 pages.
Patent Interference No. 106, 128 (DK); Judgement and File History; Jul. 26, 2021; 391 pages.
Peppermint Oil Certificate of Analysis; Printed Aug. 4, 2014; 1 page.
Porter, C. et al., "Enhancing Intestinal Drug Solubilisation Using Lipid-Based Delivery Systems", Adv Drug Del Rev., 60(6):673-91, (2008).
Porter, C. et al., "In Vitro Assessment of Oral Lipid Based Formulations", Adv Drug Deliv Rev., 50(Suppl 1):S127-47, (2001).
Porter, C. et al., "Lipid Based Formulations: Exploring the Link Between In Vitro Supersaturation and In Vivo Exposure", Bull Tech Gattefoss., 104:61-9, (2011).
Porter, C. et al., "Lipid-Based Formulations for Oral Administration: Opportunities for Bioavailability Enhancement and Lipoprotein Targeting of Lipophilic Drugs", J Recept Signal Transduct Res., 21(2-3):215-57, (2001).
Porter, C. et al., "Lymphatic Transport of Halofantrine in the Triple-Cannulated Anaesthetized Rat Model: Effect of Lipid Vehicle Digestion", J Pharm Sci., 85(4):351-6, (1996).
Porter, C. et al., "Preface: Lipid-Based Systems for the Enhanced Delivery of Poorly Water Soluble Drugs", Adv Drug Del Rev., 60(6):615-6, (2008).
Porter, C. et al., "Susceptibility to Lipase-Mediated Digestion Reduces the Oral Bioavailability of Danazol After Administration as a Medium-Chain Lipid-Based Microemulsion Formulation", Pharm Res., 21(8):1405-12, (2004).
Porter, C. et al., "Uptake of Drugs Into the Intestinal Lymphatics After Oral Administration", Adv Drug Deliv Rev., 25(1):71-89, (1997).
Porter, C. et al., "Use of In Vitro Lipid Digestion Data to Explain the In Vivo Performance of Triglyceride Based Lipid Formulations for the Oral Administration of Poorly Water-Soluble Drugs: Studies with Halofantrine", J Pharm Sci., 93(5):1110-21, (2004).
Porter, C. et al., "Lipids and Lipid-Based Formulations: Optimizing the Oral Delivery of Lipophilic Drugs", Nat Rev Drug Discov., 6(3):231-48, (2007).
Pouton, C. "Formulation of Poorly Watersoluble Drugs for Oral Administration: Physicochemical and Physiological Issues and the Lipid Formulation Classification System", Eur J Pharm Sci., 29(3-4):278-87, (2006).
Pouton, C. et al., "Self-Emulsifying Systems for Oral Delivery of Drugs", Proc Int Symp Control Rel Bioact Mater., 14:113-4, (1987).
Pouton, C. et al., "Formulation of Lipid-Based Delivery Systems for Oral Administration: Materials, Methods and Strategies", Adv Drug Del Rev., 60(6):625-37, (2008).
Pouton, C., "Assessment of the Efficiency of Self-Emulsifying Formulations", J Pharm Pharmacol., 36:51P, (1984).
Pouton, C., "Effects of the Inclusion of a Model Drug on the Performance of Self-Emulsifying Formulations", J Pharm Pharmacol., 37:1P, (1985).
Pouton, C., "Formulation of Self-Emulsifying Drug Delivery Systems", Adv Drug Del Rev., 25(1):47-58, (1997).
Pouton, C., "Key Issues When Formulating Hydrophobic Drugs with Lipids", Bull Tech Gattefosse., 92:41-50, (1999).
Pouton, C., "Lipid Formulations for Oral Administration of Drugs: Non-Emulsifying, Self-Emulsifying and 'Self-Microemulsifying' Drug Delivery Systems", Eur J Pharm Sci., 11(Suppl 2):S93-8, (2000).
Pouton, C., "Self-Emulsifying Drug Delivery Systems: Assessment of the Efficiency of Emulsification", Int J Pharm., 27(2-3):335-48, (1985).
Pouton, C., Ph.D Thesis, University of London, London, UK (1982).
Quan, D. et al., "Studies on Preparation and Absolute Bioavailability of a Self-Emulsifying System Containing Puerarin", Chem Pharm Bull. (Tokyo), 55(5):800-3, (2007).
Rajesh, B. et al., "Lipid Based Self-Emulsifying Drug Delivery System (SEDDS) for Poorly Water-Soluble Drugs: A Review", J Global Pharma Tech., 2(3):47-55, (Abstract), (2010).
Ran, Y. et al., "Prediction of Drug Solubility by the General Solubility Equation (GSE)", J Chem Inf Comput Sci., 41(2):354-7, (2001).
Ravichandiran, V. et al., "Formulation Development and Evaluation of Tamsulosin Hydrochloride and Dutasteride in Tablet Dosage Form", Der Pharmacia Sinica, 2(1):1-13 (2011).
Reddy, S. et al., "Lymphatic Transport of Orally Administered Drugs", Indian J Exp Biol., 40:1097-109, (2002).
Reddy, S. et al., "Review on Self Micro Emulsifying Drug Delivery Systems", Int J Res Pharm Sci., 2(3):382-92, (2011).
Reymond, J. et al., "In Vivo Model for Ciclosporin Intestinal Absorption in Lipid Vehicle", Pharm Res., (10):677-9, (1988).
Robinson, J., "Semi-Solid Formulations for Oral Drug Delivery", Bull Tech Gattefosse., 89:11-3, (1996).
Roth, M. et al., "Steady-State Pharmacokinetics of Oral Testosterone Undecanoate with Concomitant Inhibition of 5a-Reductase by Finasteride", Int J Androl., 34(601):541-7, (2001).
Rubenstein, A., "Gastrointestinal Anatomy, Physiology and Permeation Pathways", Enhance Drug Deliv., Ch. 1:3-35, (2006).
Rytting, E. et al., "Aqueous and Cosolvent Solubility Data for Drug-Like Organic Compounds", AAPS J., 7(1):E78-105, (2005).
Sandia Report, Enumerating Molecules, Sandia National Laboratories, Table 4, pp. 84-86 (2004).
Seal, L. "Testosterone Replacement Therapy", Medicine, 37(9):445-9, (2009).
Sek, L. et al., "Evaluation of the In-Vitro Digestion Profiles of Long and Medium Chain Glycerides and the Phase Behaviour of Their Lipolytic Products", J Pharm Pharmacol., 54(1):29-41, (2002).
Sek, L. et al., "Examination of the Impact of a Range of Pluronic Surfactants on the In Vitro Solubilisation Behaviour and Oral Bioavailability of Lipidic Formulations of Atovaquone", J Pharm Pharmacol., 58(6):809-20, (2006).
Shackleford, D. et al., "Contribution of Lymphatically Transported Testosterone Undecanoate to the Systemic Exposure of Testosterone after Oral Administration of Two Andriol Formulations in Conscious Lymph Duct-Cannulated Dogs", J Pharmacol Exp Ther., 306(3):925-33, (2003).
Shah, N. et al., "Self-Emulsifying Drug Delivery Systems (SEDDS) with Polyglycolyzed Glycerides for Improving In Vitro Dissolution and Oral Absorption of Lipophilic Drugs", Int J Pharm., 106(1):15-23, (1994).
Shen, H. et al., "Preparation and Evaluation of Self-Microemulsifying Drug Delivery Systems (SMEDDS) Containing Atorvastatin", J Pharm Pharmacol., 58(9):1183-91, (2006).
Sivak, O. et al., "Protonated Nanostructured Aluminosilicate (NSAS) Reduces Plasma Cholesterol Concentrations and Atherosclerotic Lesions in Apolipoprotein E Deficient Mice Fed a High Cholesterol and High Fat Diet", Lipids Health Dis., 8:30-4, (2009).
Solomon, L. et al., "Inhibition of Lipolysis of Medium-Chain Triglycerides by Non-ionic Surfactants, a Structure/Activity Study", Formulation of Poorly Available Drugs for Oral Administration, pp. 437-438, (1996).
Solulantm C-24 lanolin derivative (Technical Data Sheet), TDS No. 560, Lubrizol Advanced Materials, Inc., 2 pages, (revised Aug. 2005).
Stegemann, S. et al., "When Poor Solubility Becomes an Issue: From Early Stage to Proof of Concept", Eur J Pharm Sci., 31(5):249-61, (2007).
Steroid Numbering System and Nomenclature, Excerpt from Encyclopedia Britannica Online, http://_www.britannica.com/science/steroid, 5 pages, (retrieved Mar. 9, 2016).
Strickley, R., "Currently Marketed Oral Lipid-Based Dosage Forms: Drug Products and Excipients", Oral Lipid-Based Formulations: Enhancing the Bioavailability of Poorly Water-Soluble Drugs, Ch. 1, pp. 1-31, (2007).

(56) References Cited

OTHER PUBLICATIONS

Subramanian, N. et al., "Formulation Design of Self-Emulsifying Drug Delivery Systems for Improved Oral Bioavailability of Celecoxib", Biol Pharm Bull., 27(12):1993-9, (2004).
Sunesen, V. et al., "Effect of Liquid vol. and Food Intake on the Absolute Bioavailability of Danazol, A Poorly Soluble Drug", Eur J Pharm Sci., 24(4):297-303, (2005).
Swerdloff, R. et al., "Dihydrotestosterone: Biochemistry, Physiology, and Clinical Implications of Elevated Blood Levels", Endocr Rev., 38(3):220-54, (2017).
Swerdloff, R. et al., "Long-Term Pharmacokinetics of Transdermal Testosterone Gel in Hypogonadal Men", J Clin Endocrinol Metab., 85(12):4500-10, (2000).
Talegaonkar, S. et al., "Microemulsions: A Novel Approach to Enhanced Drug Delivery", Recent Pat Drug Deliv Formul., 2(3):238-57, (2008).
Tarr, B. et al., "Enhanced Intestinal Absorption of Cyclosporine in Rats Through the Reduction of Emulsion Droplet Size", Pharm Res., 6(1): 40-3, (1989).
Tenover, J., "The Androgen-Deficient Aging Male: Current Treatment Options", Rev Urol., 5(Suppl 1):S22-8, (2003).
Trull, A. et al., "Enhanced Absorption of New Oral Cyclosporin Microemulsion Formulation, Neoral, in Liver Transplant Recipients with External Biliary Diversion", Transplant Proc, 26(5):2977-8, (1994).
Tso, P. et al., "Intestinal Absorption and Lymphatic Transport of a High Linolenic Acid Canola Oil in Lymph Fistula Sprague-Dawley Rats", J Nutr. 132(2):218-21, (2002).
Tuleu, C. et al., "Comparative Bioavailability Study in Dogs of a Self-Emulsifying Formulation of Progesterone Presented in a Pellet and Liquid Form Compared with an Aqueous Suspension of Progesterone", J Pharm Sci., 93(6):1495-502, (2004).
U.S. Food and Drug Administration, Investigational New Drug Application, Drug Development and Review Definitions, 8 pages, (Mar. 8, 2016).
U.S. Appl. No. 10/159,601; Figures as filed, dated Mar. 11, 2016; 4 pages.
U.S. Appl. No. 11/196,805, filed Aug. 2, 2005; 99 pages.
U.S. Appl. No. 11/196,805; Decision of Petition, dated Apr. 16, 2015; 7 pages.
U.S. Appl. No. 11/196,805; Full File History, as of Mar. 11, 2016; 377 pages.
U.S. Appl. No. 11/196,805; Preliminary Amendment, dated Aug. 2, 2005; 8 pages.
U.S. Appl. No. 11/911,446; Applicant-Initiated Interview Summary, dated Apr. 25, 2012; 3 pages.
U.S. Appl. No. 11/911,446; Applicant-Initiated Interview Summary, dated Jun. 12, 2012; 3 pages.
U.S. Appl. No. 11/911,446; Examiner-Initiated Interview Summary, dated Dec. 27, 2010; 3 pages.
U.S. Appl. No. 11/911,446; Examiner-Initiated Interview Summary, dated Jun. 13, 2012; 1 page.
U.S. Appl. No. 11/911,446; Examiner-Initiated Interview Summary, dated Jun. 2, 2010; 3 pages.
U.S. Appl. No. 11/911,446; Examiner-Initiated Interview Summary, dated May 3, 2011; 3 pages.
U.S. Appl. No. 11/911,446; Examiner's Ammendment, dated Jun. 28, 2012; 3 pages.
U.S. Appl. No. 11/911,446; Final Office Action, dated Mar. 24, 2011; 21 pages.
U.S. Appl. No. 11/911,446; Non-Final Office Action, dated Dec. 6, 2010; 12 pages.
U.S. Appl. No. 11/911,446; Non-Final Office Action, dated May 4, 2012; 34 pages.
U.S. Appl. No. 11/911,446; Notice of Allowance, dated Jun. 28, 2012; 5 pages.
U.S. Appl. No. 12/326,711; Decision of Petition, dated Apr. 17, 2015; 7 pages.
U.S. Appl. No. 12/326,711; Full File History, as of Mar. 11, 2016; 4,139 pages.
U.S. Appl. No. 12/758,770; Applicant-Initiated Interview Summary, dated Apr. 27, 2012; 3 pages.
U.S. Appl. No. 12/758,770; Applicant-Initiated Interview Summary, dated Mar. 7, 2013; 3 pages.
U.S. Appl. No. 12/758,770; Declaration of Robert E. Dudley, Ph.D. dated Apr. 26, 2012; 10 pages.
U.S. Appl. No. 12/758,770; Examiner-Initiated Interview Summary, dated Aug. 3, 2012; 5 pages.
U.S. Appl. No. 12/758,770; Examiner-Initiated Interview Summary, dated Mar. 21, 2013; 6 pages.
U.S. Appl. No. 12/758,770; Non-Final Office Action, dated Feb. 1, 2013; 14 pages.
U.S. Appl. No. 12/758,770; Non-Final Office Action, dated Mar. 26, 2012; 14 pages.
U.S. Appl. No. 12/758,770; Notice of Allowance, dated Aug. 3, 2012; 10 pages.
U.S. Appl. No. 12/758,770; Notice of Allowance, dated Mar. 21, 2013; 6 pages.
U.S. Appl. No. 12/758,770; Response to Non-Final Office Action, dated Apr. 26, 2012; 14 pages.
U.S. Appl. No. 13/553,586; Applicant-Initiated Interview Summary, dated Jan. 31, 2014; 3 pages.
U.S. Appl. No. 13/553,586; Final Office Action, dated Aug. 26, 2016; 19 pages.
U.S. Appl. No. 13/553,586; Final Office Action, dated Nov. 5, 2013; 17 pages.
U.S. Appl. No. 13/553,586; Non-Final Office Action, dated Apr. 9, 2015; 18 pages.
U.S. Appl. No. 13/553,586; Non-Final Office Action, dated Jan. 25, 2016; 10 pages.
U.S. Appl. No. 13/553,586; Non-Final Office Action, dated Mar. 5, 2013; 14 pages.
U.S. Appl. No. 13/553,586; Notice of Allowance, dated Jun. 3, 2014; 5 pages.
U.S. Appl. No. 13/553,586; Notice of Appeal, dated Feb. 24, 2017; 2 pages.
U.S. Appl. No. 13/553,586; Response to Non-Final Office Action, dated Jun. 4, 2013; 14 pages.
U.S. Appl. No. 13/584,958; Final Office Action, dated Jan. 31, 2014; 4 pages.
U.S. Appl. No. 13/584,958; Non-Final Office Action, dated Nov. 8, 2013; 9 pages.
U.S. Appl. No. 13/584,958; Notice of Allowance, dated Apr. 14, 2014; 5 pages.
U.S. Appl. No. 13/592,258; (Giliyar et al., Publication date: Dec. 20, 2012).
U.S. Appl. No. 13/663,352; (Fikstad et al., Publication date: Feb. 28, 2013).
U.S. Appl. No. 13/843,403; Final Office Action, dated May 27, 2014; 32 pages.
U.S. Appl. No. 13/843,403; 3416 pages.
U.S. Appl. No. 14/026,655; Non-Final Office Action, dated Mar. 20, 2014; 10 pages.
U.S. Appl. No. 14/216,240; Final Office Action, dated Dec. 15, 2016; 14 pages.
U.S. Appl. No. 14/216,240; Final Office Action, dated May 27, 2015; 13 pages.
U.S. Appl. No. 14/216,240; Non-Final Office Action, dated Apr. 28, 2016; 13 pages.
U.S. Appl. No. 14/216,240; Non-Final Office Action, dated Dec. 24, 2014; 11 pages.
U.S. Appl. No. 14/254,545; Final Office Action, dated Jul. 15, 2014; 8 pages.
U.S. Appl. No. 14/254,545; Non-Final Office Action, dated Jun. 13, 2014; 13 pages.
U.S. Appl. No. 14/254,545; Notice of Allowance, dated Jul. 29, 2014; 5 pages.
U.S. Appl. No. 14/290,540; Final Office Action, dated Jun. 17, 2016; 10 pages.
U.S. Appl. No. 14/290,540; Non-Final Office Action, dated Sep. 17, 2015; 8 pages.
U.S. Appl. No. 14/291,172; 467 pages.
U.S. Appl. No. 14/292,615; 1992 pages.

(56) References Cited

OTHER PUBLICATIONS

U.S. Appl. No. 14/303,179; Final Office Action, dated Dec. 31, 2015; 13 pages.
U.S. Appl. No. 14/303,179; Final Office Action, dated Jun. 1, 2017; 15 pages.
U.S. Appl. No. 14/303,179; Non-Final Office Action, dated Aug. 16, 2016; 18 pages.
U.S. Appl. No. 14/303,179; Non-Final Office Action, dated Jan. 13, 2016; 13 pages.
U.S. Appl. No. 14/303,179; Non-Final Office Action, dated Jun. 16, 2015; 9 pages.
U.S. Appl. No. 14/303,179; Non-Final Office Action, dated Sep. 17, 2015; 11 pages.
U.S. Appl. No. 14/303,179; Notice of Appeal, dated Jan. 27, 2017; 2 pages.
U.S. Appl. No. 14/319,051; 676 pages.
U.S. Appl. No. 14/319,077; 770 pages.
U.S. Appl. No. 14/460,188; Decision of Petition, dated May 7, 2015; 15 pages.
U.S. Appl. No. 14/460,188; Full File History, as of Mar. 11, 2016; 186 pages.
U.S. Appl. No. 14/713,692.
U.S. Appl. No. 14/713,692; Pending Claims, filed on Sep. 2, 2015; 1 page.
U.S. Appl. No. 14/713,692; Preliminary Amendment as filed, dated May 15, 2015; 33 pages.
U.S. Appl. No. 14/820,749; Final Office Action, dated Dec. 21, 2016; 15 pages.
U.S. Appl. No. 14/820,749; Non-Final Office Action, dated Jun. 3, 2016; 14 pages.
U.S. Appl. No. 14/820,749; Notice of Appeal, dated Jun. 20, 2017; 2 pages.
U.S. Appl. No. 14/820,756; Final Office Action, dated Jul. 28, 2016; 25 pages.
U.S. Appl. No. 14/820,761; Final Office Action, dated Jul. 28, 2016; 25 pages.
U.S. Appl. No. 14/820,761; Non-Final Office Action, dated Jan. 12, 2016; 13 pages.
U.S. Appl. No. 14/820,761; Non-Final Office Action, dated Sep. 17, 2015; 11 pages.
U.S. Appl. No. 14/820,761; Notice of Appeal, dated Jan. 27, 2017; 2 pages.
U.S. Appl. No. 14/820,765; Final Office Action, dated Jul. 29, 2016; 29 pages.
U.S. Appl. No. 14/820,765; Non-Final Office Action, dated Jan. 13, 2016; 16 pages.
U.S. Appl. No. 14/820,765; Non-Final Office Action, dated Sep. 18, 2015; 11 pages.
U.S. Appl. No. 14/820,765; Notice of Appeal, dated Jan. 27, 2017; 2 pages.
U.S. Appl. No. 15/381,430; Non-Final Office Action, dated Aug. 19, 2019; pages.
U.S. Appl. No. 15/381,430; Non-Final Office Action, dated Feb. 27, 2018; 14 pages.
U.S. Appl. No. 15/381,430; Non-Final Office Action, dated May 11, 2017; 13 pages.
U.S. Appl. No. 15/381,430; Notice of Allowance, dated Jan. 10, 2020; 25 pages.
U.S. Appl. No. 15/458,240; Final Office Action, dated Sep. 21, 2018; 25 pages.
U.S. Appl. No. 15/458,240; Non-Final Office Action, dated Feb. 7, 2018; 13 pages.
U.S. Appl. No. 15/723,955; Applicant-Initiated Interview Summary, dated Dec. 20, 2018; 3 pages.
U.S. Appl. No. 15/723,955; Final Office Action, dated Jun. 1, 2018; 25 pages.
U.S. Appl. No. 15/723,955; Final Office Action, dated May 15, 2019; 29 pages.
U.S. Appl. No. 15/723,955; Non-Final Office Action, dated Jan. 10, 2020; 28 pages.
U.S. Appl. No. 15/723,955; Non-Final Office Action, dated Nov. 5, 2018; 27 pages.
U.S. Appl. No. 15/723,955; Pending claims from 3rd Party Observation (Exhibit C-1), dated Dec. 11, 2019; 4 pages.
U.S. Appl. No. 15/723,963; Applicant-Initiated Interview Summary, dated Apr. 18, 2018; 3 pages.
U.S. Appl. No. 15/723,963; Final Office Action, dated Jun. 1, 2018; 25 pages.
U.S. Appl. No. 15/723,970; Applicant-Initiated Interview Summary, dated Apr. 18, 2018; 3 pages.
U.S. Appl. No. 15/723,970; Final Office Action, dated Jun. 1, 2018; 25 pages.
U.S. Appl. No. 15/723,976; Allowed claims from 3rd Party Observation (Exhibit B-1), dated Dec. 11, 2019; 3 pages.
U.S. Appl. No. 15/723,976; Applicant-Initiated Interview Summary, dated Dec. 20, 2018; 3 pages.
U.S. Appl. No. 15/723,976; Final Office Action, dated Apr. 17, 2019; 24 pages.
U.S. Appl. No. 15/723,976; Final Office Action, dated Jun. 25, 2018; 28 pages.
U.S. Appl. No. 15/723,976; Non-Final Office Action, dated Nov. 5, 2018; 28 pages.
U.S. Appl. No. 15/723,976; Notice of Allowance, dated Nov. 14, 2019; 15 pages.
U.S. Appl. No. 15/723,976; Pre-Interview First Office Action, dated Jan. 16, 2018; 3 pages.
U.S. Appl. No. 15/723,985; Final Office Action, dated Aug. 8, 2019; 16 pages.
U.S. Appl. No. 15/723,985; Non-Final Office Action, dated Feb. 13, 2019; 25 pages.
U.S. Appl. No. 15/723,985; Pre-Interview First Office Action, dated Feb. 20, 2018; 4 pages.
U.S. Appl. No. 15/814,162; Non-Final Office Action, dated Aug. 9; 2019; 24 pages.
U.S. Appl. No. 15/814,162; Non-Final Office Action, dated Jan. 16, 2018; 9 pages.
U.S. Appl. No. 15/814,162; Notice of Allowance, dated Oct. 6, 2021; 13 pages.
U.S. Appl. No. 15/984,028; Non-Final Office Action, dated Sep. 7, 2018; 5 pages.
U.S. Appl. No. 16/183,155; Non-Final Office Action, dated Jan. 8, 2021; 22 pages.
U.S. Appl. No. 16/183,155; Non-Final Office Action, dated Mar. 6, 2020; 43 pages.
U.S. Appl. No. 16/295,427; Non-Final Office Action, dated May 13, 2021; 29 pages.
U.S. Appl. No. 16/295,427; Non-Final Office Action, dated Nov. 15, 2019; 22 pages.
U.S. Appl. No. 16/360,583; Non-Final Office Action, dated Feb. 24, 2020; 13 pages.
U.S. Appl. No. 16/656,157; Final Office Action, dated Aug. 18, 2020; 36 pages.
U.S. Appl. No. 16/656,157; Non-Final Office Action, dated Jan. 28, 2020; 46 pages.
U.S. Appl. No. 16/656,157; Notice of Allowance, dated Oct. 6, 2021; 17 pages.
U.S. Appl. No. 16/656,169; Final Office Action, dated Sep. 17, 2020; 23 pages.
U.S. Appl. No. 16/656,169; Non-Final Office Action, dated Mar. 6, 2020; 41 pages.
U.S. Appl. No. 16/656,169; Non-Final Office Action, dated Oct. 5, 2021; 17 pages.
U.S. Appl. No. 16/656,169; Notice of Allowance, dated Dec. 10, 2020; 11 pages.
U.S. Appl. No. 16/656,169; Notice of Allowance, dated Dec. 10, 2020; 12 pages.
U.S. Appl. No. 16/656,178; Final Office Action, dated Sep. 16, 2020; 23 pages.
U.S. Appl. No. 16/656,178; Non-Final Office Action, dated Feb. 27, 2020; 38 pages.
U.S. Appl. No. 16/656,178; Notice of Allowance, dated Nov. 16, 2020; 8 pages.

(56) References Cited

OTHER PUBLICATIONS

U.S. Appl. No. 16/656,178; Protest under 37 CFR § 1.291, dated Dec. 11, 2019; 14 pages.
U.S. Appl. No. 16/720,183. filed Dec. 19, 2019; 49 pages.
U.S. Appl. No. 16/720,183; Final Office Action, dated Oct. 15, 2020; 17 pages.
U.S. Appl. No. 16/720,183; Non-Final Office Action, dated May 14, 2020; 12 pages.
U.S. Appl. No. 16/720,194, filed Dec. 19, 2019; 49 pages.
U.S. Appl. No. 16/720,194; Final Office Action, dated Oct. 20, 2020; 23 pages.
U.S. Appl. No. 16/720,194; Non-Final Office Action, dated May 14, 2020; 13 pages.
Vertzoni, M. et al., "Dissolution Media Simulating the Intralumenal Composition of the Small Intestine: Physiological Issues and Practical Aspects", J Pharm Pharmacol., 56(4):453-62, (2004).
Wacher, V. et al., Peppermint Oil Enhances Cyclosporine Oral Bioavailability in Rats: Comparison with D-a-Tocopheryl Poly(ethylene glycol 1000) Succinate (TPGS) and Ketoconazole, J Pharm Sci., 91(1):77-90, (2002).
Wakerly, M. et al., "Evaluation of the Self-Emulsifying Performance of a Non-Ionic Surfactant-Vegetable Oil Mixture", J Pharm Pharmacol., 39:p. 6, (1987).
Wakerly, M. et al., "Self-Emulsification of Vegetable Oil-Nonionic Surfactant Mixtures: A Proposed Mechanism of Action", ACS, 311(18):242-55, (1986).
Wakerly, M. et al., "The Effect of Surfactant HLB on the Self-Emulsifying Efficiency of Non-Ionic Surfactant Vegetable Oil Mixtures", J Pharm Pharmacol., 38(S12):p. 2, (1986).
Wakerly, M., "Self-Emulsifying Drug Delivery Systems Based on Nonionic Surfactant-Oil Mixtures", Ph.D. Thesis, University of Bath, Bath, UK, (1989).
WHO, "Guidelines for the Use of Androgens in Men", Special Programme of Research, Development and Research Training in Human Reproduction, 73 pages, (1992).
Wong, C. et al., "Carboxylesterases 1 and 2 Hydrolyze Phospho-Nonsteroidal Anti-Inflammatory Drugs: Relevance to Their Pharmacological Activity", J Pharmacol Exp Ther., 340(2):422-32, (2012).
Xie, G. et al., "In Vitro and In Vivo Metabolic Studies of Phospho-Aspirin (MDC-22)", Pharm Res., 29(12):3292-301, (2012).
Xie, G. et al., "Regioselective Oxidation of Phospho-NSAIDs by Human Cytochrome P450 and Flavin Monooxygenase Isoforms: Implications for their Pharmacokinetic Properties and Safety", Br J Pharmacol., 167(1):222-32, (2012).
Yalkowsky, "Solubilization by Surfactants", Chapter 6, pp. 236-320, in Solubility and Solubilization in Aqueous Media, American Chemical Society, Oxford Univ. Press: New York, NY (1999).
Yalkowsky, S. et al., "Solubility and Partitioning 1: Solubility of Nonelectrolytes in Water", J Pharm Sci., 69(8):912-7, (1980).
Yanez, J. et al., "Intestinal Lymphatic Transport for Drug Delivery", Adv Drug Deliv Rev., 63(10-11):923-42, (2011).
Yap, S. et al., "Influence of Lipolysis and Droplet Size on Tocotrienol Absorption from Self-Emulsifying Formulations", Int J Pharm., 281(1-2):67-78, (2004).
Yin, A. et al., "Dietary Fat Modulates the Testosterone Pharmacokinetics of a New Self-Emulsifying Formulation of Oral Testosterone Undecanoate in Hypogonadal Men", J Androl., 33(6):1282-90, (2012).
Yin, A. et al., "Reexamination of Pharmacokinetics of Oral Testosterone Undecanoate in Hypogonadal Men With a New Self-Emulsifying Formulation", J Androl., 33(2):190-201, (2012).
Zangenberg, N. et al., "A Dynamic In Vitro Lipolysis Model. II: Evaluation of the Model", Eur J Pharm Sci., 14(3):237-44, (2001).
Zhu, C. et al., "Phosphosulindac (OXT-328) Selectively Targets Breast Cancer Stem Cells in Vitro and in Human Breast Cancer Xenografts", Stem Cells, 30(10):2065-75, (2012).
Zhu, R. et al., "Phospho-Sulindac (OXT-328) Inhibits the Growth of Human Lung Cancer Xenografts in Mice: Enhanced Efficacy and Mitochondria Targeting by its Formulation in Solid Lipid Nanoparticles", Pharm Res., 29(11):3090-101, (2012).
Anaissie, J., et al. "Testosterone Replacement Therapy and Components of the Metabolic Syndrome," Sex Med Rev, 1011 (2017).
Dalmasso, C. et al. "Cardiovascular and Metabolic Consequences of Testosterone Supplements in Young and Old Male Spontaneously Hypertensive Rats: Implications for Testosterone Supplements in Men," J Am Heart Assoc, 1-10, (2017).
Fernandez-Balsells et al. "Adverse Effects of Testosterone Therapy in Adult Men: A Systematic Review and Meta-Analysis," J. Clin. Endocrinol. Metab., 95(6):2560-2575, (2010).
Gonzalez, J. et al. "Testosterone Replacement and Cardiovascular Disease Risk: What do Endocronologists Need to Know?", Cardiovasc. Endocrinol., 4(3): 100-107, (2015).
Ohlsson et al. "High Serum Testosterone Is Associated With Reduced Risk of Cardiovascular Events in Elderly Men," Journal of the American College of Cardiology, vol. 58, No. 16, 2011, pp. 1674-1681.
Precirol ATO 5®, http://www.thanch.com/en/cp.asp?id=597, accessed on Feb. 16, 2017, 1 page.
Reckelhoff, et al. "Testosterone Exacerbates Hypertension and Reduces Pressure-Natriuresis in Male Spontaneously Hypertensive Rats", Hypertension, vol. 31, No. 1, 1998, pp. 435-439.
Velho, I. et al. "Effects of Testosterone Therapy on BMI, Blood Pressure, and Laboratory Profile of Transgender Men: A Systematic Review," Andrology, 5:881-888, (2017).
Vemula et al., "Lipid Based Self-Emulsifying Drug Delivery System (SEDDS) for Poorly Water-Soluble Drugs: A Review," Journal of Global Pharmaceutical Tehcnol., vol. 2, No. 3, 2010, pp. 47-55. Abstract only.
Vikan, et al. "Endogenous Sex Hormones and the Prospective Association with Cardiovascular Disease and Mortality in Men, The Tromsø Study", European Society of Endocrinology, 2009, 26 pages.
Zitzmann, M., et al. "Androgen Receptor Gene CAG Repeat Length and Body Mass Index Modulate the Safety of Long-Term Intramuscular Testosterone Undecanoate Therapy in Hypogonadal Men," J. of Clin. Endocrinology & Metabolism, 92(10):3844-3853, (2007).
U.S. Appl. No. 62/782,865, filed Dec. 20, 2018, Dudley et al.
U.S. Appl. No. 18/451,557, filed Aug. 17, 2023, Dudley et al.

FIG. 2

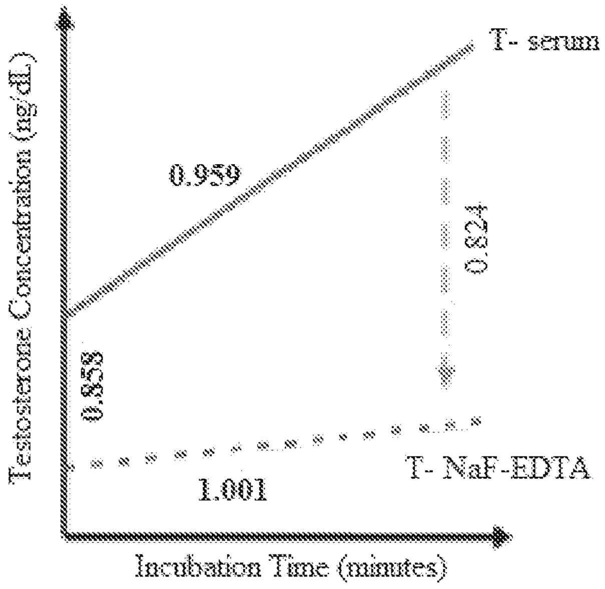

T-Serum = Testosterone concentration as measured in serum from blood stored in a plain tube at room temperature for 30 minutes T-NaF-EDTA = Testosterone concentration as measured in plasma from blood stored in a NaF-EDTA tube on ice for 30 minutes = TU to T conversion during 30 minute clotting time = TU to T conversion while on ice for 30 minutes = Net, combined effect of stages on concentrations

Bold values adjust T concentrations between stages

METHODS OF TREATING TESTOSTERONE DEFICIENCY

This application is a continuation of U.S. application Ser. No. 16/720,194, filed Dec. 19, 2019, which claims priority to U.S. provisional application No. 62/782,865, filed Dec. 20, 2018, the disclosures of which are incorporated by reference herein in their entireties.

Provided are treatments for testosterone deficiency and methods utilizing oral formulations of testosterone undecanoate that optimize the serum testosterone concentration during chronic treatment.

Testosterone (T) is a primary androgenic hormone produced in the interstitial cells of the testes and is responsible for normal growth, development and maintenance of male sex organs and secondary sex characteristics (e.g., deepening voice, muscular development, facial hair, etc.). Throughout adult life, testosterone is necessary for proper functioning of the testes and its accessory structures, prostate and seminal vesicle; for sense of well-being; and for maintenance of libido, erectile potency.

Testosterone deficiency—insufficient secretion of T characterized by low total T concentrations—can give rise to medical conditions (e.g., hypogonadism) in males. Symptoms associated with male hypogonadism include impotence and decreased sexual desire, fatigue and loss of energy, mood depression, regression of secondary sexual characteristics, decreased muscle mass, and increased fat mass. Furthermore, hypogonadism in men is a risk factor for osteoporosis, metabolic syndrome, type II diabetes and cardiovascular disease.

Various testosterone replacement therapies are commercially available for the treatment of male hypogonadism. Pharmaceutical preparations include both testosterone and testosterone derivatives in the form of intramuscular injections, implants, oral tablets of alkylated T (e.g., methyltestosterone), topical gels, topical patches, or an intranasal gel. Over time, however, the current methods of treating testosterone deficiency suffer from poor compliance and thus unsatisfactory treatment of men with low T. For example, in a recently published study, patient adherence to topical T replacement therapy at 6 months was only 34.7% and by 12 months, only 15.4% of patients continued on topical T therapy (Medication Adherence and Treatment Patterns for Hypogonadal Patients Treated with Topical Testosterone Therapy: A Retrospective Medical Claims Analysis. Michael Jay Schoenfeld, Emily Shortridge, Zhanglin Cui and David Muram, Journal of Sexual Medicine March 2013).

Various testosterone replacement therapies are commercially available for the treatment of male hypogonadism. Pharmaceutical preparations include both testosterone and testosterone derivatives in the form of intramuscular injections, implants, oral tablets of alkylated T (e.g., methyltestosterone), topical gels, topical patches, or an intranasal gel.

Despite the advances that have been made in this field, there remains a need for new therapeutic products useful to treatment of testosterone deficiency. One such agent is testosterone undecanoate, which has the following chemical structure:

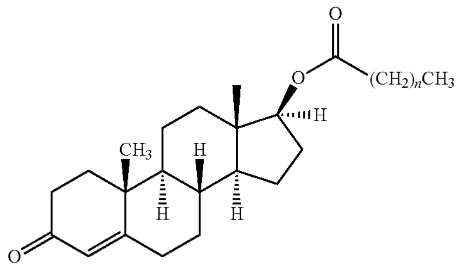

A formulation of testosterone undecanoate has been reported in the FDA approved drug label JATENZO®. The formulation also includes oleic acid, polyoxyl 40 hydrogenated castor oil (Cremophor RH 40), borage seed oil, peppermint oil, and butylated hydroxytoluene.

There is a significant, unmet need for methods for treating of testosterone deficiency. The present disclosure fulfills these and other needs, as evident in reference to the following disclosure.

Provided is a method of treating conditions associated with a deficiency or absence of endogenous testosterone in a subject in need thereof comprising the steps of:

- administering to the subject a defined dose of an oral pharmaceutical composition comprising testosterone undecanoate solubilized in a carrier comprising at least one lipophilic surfactant and at least one hydrophilic surfactant;
- collecting a blood sample from the subject;
- measuring the serum testosterone concentration in the subject; and
- increasing the dose of testosterone undecanoate when the measured serum testosterone concentration in the subject is less than about 425 ng/dL,
- decreasing the dose of testosterone undecanoate when the measured serum testosterone concentration in the subject is greater than about 970 ng/dL, or
- maintaining the dose of testosterone undecanoate when the measured serum testosterone concentration in the subject is between about 425 ng/dL and about 970 ng/dL.

Also provided is a method of treating chronic testosterone deficiency in a subject in need thereof comprising the steps of:

- administering daily to the subject a defined dose of an oral pharmaceutical composition comprising testosterone undecanoate solubilized in a carrier comprising at least one lipophilic surfactant and at least one hydrophilic surfactant;
- measuring the circulating testosterone concentration in the subject from which blood is collected; and
- increasing the dose of testosterone undecanoate when the measured serum testosterone C6 (i.e., serum T concentration in a blood sample drawn 6 hours post an oral TU dose) in the subject is less than about 425 ng/dL, decreasing each dose of testosterone undecanoate administered when the serum testosterone C6 in the subject is greater than about 970 ng/dL, and maintaining each dose of testosterone undecanoate administered when the measured serum testosterone C6 in the subject is between about 425 ng/dL and about 970 ng/dL.

Also provided is a method of treating chronic testosterone deficiency in a subject in need thereof comprising the steps of:

administering daily to the subject a defined dose of an oral pharmaceutical composition comprising testosterone undecanoate solubilized in a carrier comprising at least one lipophilic surfactant and at least one hydrophilic surfactant;

collecting the subject's blood sample;

measuring the serum testosterone concentration in the subject;

making a titration decision based on the measured serum testosterone concentration; and increasing the dose of testosterone undecanoate administered when the measured serum testosterone concentration in the subject is less than about 425 ng/dL, decreasing each dose of testosterone undecanoate administered when the measured serum testosterone concentration in the subject is greater than about 970 ng/dL, and maintaining each dose of testosterone undecanoate administered when the measured serum testosterone concentration in the subject is between about 425 ng/dL and about 970 ng/dL.

Also provided is a method of treating chronic testosterone deficiency in a subject in need thereof comprising the steps of:

administering to the subject a first dose of an oral pharmaceutical composition comprising a 237 mg dose of testosterone undecanoate (TU) solubilized in a carrier comprising at least one lipophilic surfactant and at least one hydrophilic surfactant;

after a first time period, measuring the subject's testosterone concentration; and increasing the dose of testosterone undecanoate administered when the measured serum testosterone concentration is less than about 425 ng/dL, decreasing the dose of testosterone undecanoate administered when the measured serum testosterone concentration is greater than about 970 ng/dL, and maintaining the dose of testosterone undecanoate administered when the measured serum testosterone concentration in the subject is between about 425 ng/dL and about 970 ng/dL.

Also provided is a method of treating chronic testosterone deficiency in a subject in need thereof comprising the steps of:

administering twice daily (BID) to the subject an oral pharmaceutical composition comprising a 237 mg dose of testosterone undecanoate (TU) solubilized in a carrier comprising at least one lipophilic surfactant and at least one hydrophilic surfactant;

collecting the subject's blood sample six hours after administration of the morning dose;

measuring the serum testosterone concentration in the subject 6 hours after the morning dose; and increasing the dose of testosterone undecanoate administered when the measured serum testosterone concentration in the subject is less than about 425 ng/dL, decreasing each dose of testosterone undecanoate administered when the measured serum testosterone concentration in the subject is greater than about 970 ng/dL, and maintaining each dose of testosterone undecanoate administered when the measured serum testosterone concentration in the subject is between about 425 ng/dL and about 970 ng/dL.

Also provided is a method of measuring a subject's testosterone concentration comprising:

collecting the subject's blood sample and obtaining the serum from the blood sample;

measuring the subject's serum testosterone concentration; and estimating the subject's blood testosterone concentration by measuring the subject's serum testosterone concentration and dividing that concentration by a conversion factor.

Disclosed herein is a method of treating conditions associated with a deficiency or absence of endogenous testosterone in a subject in need thereof comprising the steps of:

i. administering to the subject a defined dose of an oral pharmaceutical composition comprising testosterone undecanoate solubilized in a carrier comprising at least one lipophilic surfactant and at least one hydrophilic surfactant, wherein the defined dose is 237 mg administered twice daily;
ii. collecting a blood sample from the subject;
iii. measuring the serum testosterone concentration in the subject; and
iv. increasing the dose of testosterone undecanoate to 316 mg, administered twice daily, when the measured serum testosterone concentration in the subject is less than about 425 ng/dL,
V. decreasing the dose of testosterone undecanoate to 198 mg, administered twice daily, when the measured serum testosterone concentration in the subject is greater than about 970 ng/dL, or
vi. maintaining the dose of testosterone undecanoate when the measured serum testosterone concentration in the subject is between about 425 ng/dL and about 970 ng/dL.

Disclosed herein is a method of treating conditions associated with a deficiency or absence of endogenous testosterone in a subject in need thereof comprising the steps of:

i. administering to the subject a defined dose of an oral pharmaceutical composition comprising testosterone undecanoate solubilized in a carrier comprising at least one lipophilic surfactant and at least one hydrophilic surfactant, wherein the defined dose is 316 mg administered twice daily;
ii. collecting a blood sample from the subject;
iii. measuring the serum testosterone concentration in the subject; and
iv. increasing the dose of testosterone undecanoate to 396 mg, administered twice daily, when the measured serum testosterone concentration in the subject is less than about 425 ng/dL,
v. decreasing the dose of testosterone undecanoate to 237 mg, administered twice daily, when the measured serum testosterone concentration in the subject is greater than about 970 ng/dL, or
vi. maintaining the dose of testosterone undecanoate when the measured serum testosterone concentration in the subject is between about 425 ng/dL and about 970 ng/dL.

Disclosed herein is a method of treating conditions associated with a deficiency or absence of endogenous testosterone in a subject in need thereof comprising the steps of:

i. administering to the subject a defined dose of an oral pharmaceutical composition comprising testosterone undecanoate solubilized in a carrier comprising at least one lipophilic surfactant and at least one hydrophilic surfactant, wherein the defined dose is 198 mg administered twice daily;
ii. collecting a blood sample from the subject;
iii. measuring the serum testosterone concentration in the subject; and iv. increasing the dose of testosterone undecanoate to 237 mg, administered twice daily, when the measured serum testosterone concentration in the subject is less than about 425 ng/dL, v. decreasing the dose of testosterone undecanoate to 158 mg, administered twice daily, when the measured serum testosterone concentration in the subject is greater than about 970 ng/dL, or vi. maintaining the dose of testosterone undecanoate when the measured serum testosterone concentration in the subject is between about 425 ng/dL and about 970 ng/dL.

Disclosed herein is a method of treating conditions associated with a deficiency or absence of endogenous testosterone in a subject in need thereof comprising the steps of:

i. administering to the subject a defined dose of an oral pharmaceutical composition comprising testosterone undecanoate solubilized in a carrier comprising at least one lipophilic surfactant and at least one hydrophilic surfactant, wherein the defined dose is 396 mg administered twice daily;

ii. collecting a blood sample from the subject;

iii. measuring the serum testosterone concentration in the subject; and iv. decreasing the dose of testosterone undecanoate to 316 mg, administered twice daily, when the measured serum testosterone concentration in the subject is greater than about 970 ng/dL, or v. maintaining the dose of testosterone undecanoate when the measured serum testosterone concentration in the subject is between about 425 ng/dL and about 970 ng/dL.

Disclosed herein is a method of treating conditions associated with a deficiency or absence of endogenous testosterone in a subject in need thereof comprising the steps of:

i. administering to the subject a defined dose of an oral pharmaceutical composition comprising testosterone undecanoate solubilized in a carrier comprising at least one lipophilic surfactant and at least one hydrophilic surfactant, wherein the defined dose is 158 mg administered twice daily;

ii. collecting a blood sample from the subject;

iii. measuring the serum testosterone concentration in the subject; and iv. increasing the dose of testosterone undecanoate to 198 mg, administered twice daily, when the measured serum testosterone concentration in the subject is less than about 425 ng/dL, and v. treatment is discontinued when the subject's measured serum testosterone concentration in the subject is greater than about 970 ng/dL.

In an embodiment, said serum testosterone concentration is measured four to eight hours after administering the oral pharmaceutical composition.

In an embodiment, said serum testosterone concentration at 6 hours after administration of the morning dose is used to approximate $C_{avg}$.

In an embodiment, said oral pharmaceutical composition comprises about 19.8 percent by weight of solubilized testosterone undecanoate, about 51.6 percent by weight of oleic acid, and about 16.1 percent by weight of polyoxyethylene (40) hydrogenated castor oil.

In an embodiment, said oral pharmaceutical composition further comprises about 10 percent by weight of borage seed oil and about 2.5 percent by weight of peppermint oil.

In an embodiment, said oral pharmaceutical composition comprises about 15 percent by weight of solubilized testosterone undecanoate; about 16 percent by weight of polyoxyethylene (40) hydrogenated castor oil; about 63 percent by weight of glyceryl monolinoleate; and about 6 percent by weight of polyethylene glycol 8000.

In an embodiment, said testosterone concentrations are measured in serum from a blood sample collected in a plain tube drawn 5-7 hours after the morning dose and at least 7 days after starting treatment and following dose adjustment.

In an embodiment, said subject is diagnosed with hypogonadal conditions associated with structural or genetic etiologies.

In an embodiment, said subject is diagnosed with primary hypogonadism.

In an embodiment, said subject is diagnosed with testicular failure due to cryptorchidism, bilateral torsion, orchitis, vanishing testis syndrome, orchiectomy, Klinefelter syndrome, chemotherapy, or toxic damage from alcohol or heavy metals.

In an embodiment, said subject is diagnosed with hypogonadotropic hypogonadism.

In an embodiment, said subject is diagnosed with gonadotropin or luteinizing hormone-releasing hormone (LHRH) deficiency or pituitary-hypothalamic injury from tumors, trauma, or radiation.

In an embodiment, said subject is not diagnosed with age-related hypogonadism.

In an embodiment, wherein prior to administering the defined dose of an oral pharmaceutical composition, further comprising the step of confirming the diagnosis of hypogonadism.

In an embodiment, said diagnosis of hypogonadism is confirmed if the serum testosterone concentrations measured on at least two separate days are below the normal range.

BRIEF DESCRIPTION OF THE DRAWINGS

FIG. 2 shows the relationship between multiple effects on the T concentration and an overall conversion factor that can be used to translate the T concentration in one setting to an equivalent, actionable T concentration in a second setting.

DETAILED DESCRIPTION

Abbreviations and Definitions

Figure 1:
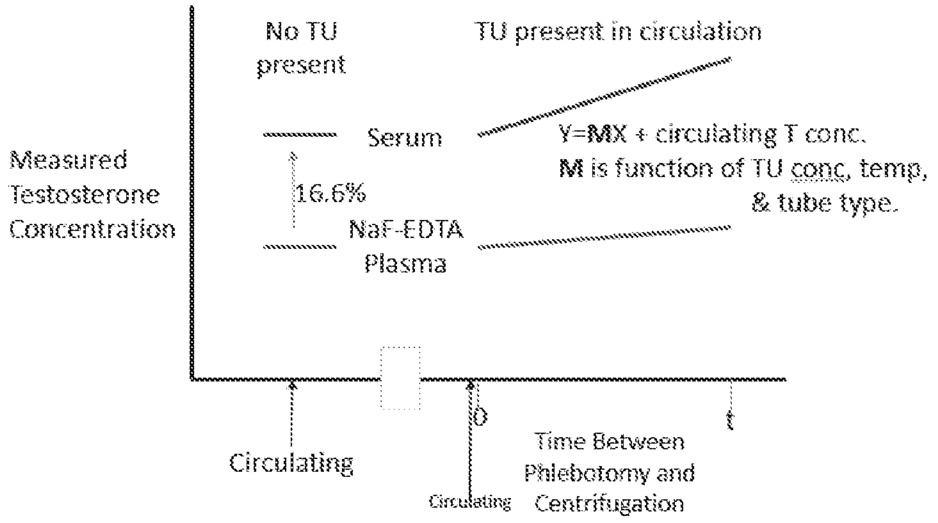
FIG. 1 shows a schematic of the difference in T concentrations measured in serum and NaF-EDTA Plasma.

To facilitate understanding, a number of terms and abbreviations as used herein are defined below as follows:

When introducing elements of the present invention or the particular embodiment(s) thereof, the articles "a", "an", "the" and "said" are intended to mean that there are one or more of the elements. The terms "comprising", "including" and "having" are intended to be inclusive and mean that there may be additional elements other than the listed elements.

The term "and/or" when used in a list of two or more items, means that any one of the listed items can be employed by itself or in combination with any one or more of the listed items. For example, the expression "A and/or B" is intended to mean either or both of A and B, i.e. A alone, B alone or A and B in combination. The expression "A, B and/or C" is intended to mean A alone, B alone, C alone, A and B in combination, A and C in combination, B and C in combination or A, B, and C in combination.

The term "about," as used herein, is intended to qualify the numerical values that it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

The term "plasma," as used herein, is intended to mean the liquid component of blood that holds the blood cells in whole blood in suspension; this makes plasma the extracellular matrix of blood cells. It makes up about 55% of the body's total blood volume. It is mostly water (up to 95% by volume), and contains dissolved proteins (6-8%) (i.e.—serum albumins, globulins, and fibrinogen), glucose, clotting factors, electrolytes (Nat, $Ca^{2+}$, $Mg^{2+}$, $HCO_3^-$, Cl, etc.), hormones, carbon dioxide (plasma being the main medium for excretory product transportation) and oxygen. This is in contrast to blood serum which is blood plasma without clotting factors. Further, plasma is derived from blood that is collected differently than when serum is collected, by allowing the blood to clot prior to centrifugation when collecting serum versus immediate centrifugation when collecting plasma.

The phrase "conditions associated with a deficiency or absence of endogenous testosterone" or "chronic testosterone deficiency," as used herein, is intended to refer to:

- Primary hypogonadism (congenital or acquired): testicular failure due to cryptorchidism, bilateral torsion, orchitis, vanishing testis syndrome, orchiectomy, Klinefelter syndrome, chemotherapy, or toxic damage from alcohol or heavy metals. These men usually have low serum testosterone concentrations and gonadotropins (follicle-stimulating hormone [FSH], luteinizing hormone [LH]) above the normal range; and
- Hypogonadotropic hypogonadism (congenital or acquired): gonadotropin or luteinizing hormone-releasing hormone (LHRH) deficiency or pituitary-hypothalamic injury from tumors, trauma, or radiation. These men have low testosterone serum concentrations but have gonadotropins in the normal or low range.

The term "normal range" or "eugonadal range" as used herein, is intended to mean an average steady state plasma levels (concentrations) of testosterone of about 300-1100 ng/dL.

The term "lipophilic surfactant," as used herein is intended to mean a surfactant having a hydrophilic-lipophilic balance (HLB) less than 10, such as less than 5, for example, 1 to 2. Certain lipophilic surfactants suitable in oral compositions described herein include fatty acids ($C_6$-$C_{24}$, such as $C_{10}$-$C_{24}$, for example $C_{14}$-$C_{24}$), for example, octanoic acid, decanoic acid, undecanoic acid, lauric acid, myristic acid, palmitic acid, palmitoleic, stearic acid, oleic acid, linoleic acid, alpha- and gamma-linolenic acid, arachidonic acid or combinations thereof. In some embodiments, the lipophilic surfactant is oleic acid. In some embodiments, the lipophilic surfactant is glyceryl monolinoleate.

Other lipophilic surfactants include:

- Mono- and/or di-glycerides of fatty acids, such as glyceryl distearate, Imwitor 988 (glyceryl mono-/di-caprylate), Imwitor 742 (glyceryl mono-di-caprylate/caprate), Imwitor 308 (glyceryl mono-caprylate), Imwitor 191 (glyceryl mono-stearate), Softigen 701 (glyceryl mono-/di-ricinoleate), Capmul MCM (glyceryl caprylate/caprate), Capmul MCM (L) (liquid form of Capmul MCM), Capmul GMO (glyceryl mono-oleate), Capmul GDL (glyceryl dilaurate), Maisine (glyceryl mono-linoleate), Peceol (glyceryl mono-oleate), Myverol 18-92 (distilled monoglycerides from sunflower oil) and Myverol 18-06 (distilled monoglycerides from hydrogenated soybean oil), Precirol ATO 5 (glyceryl palmitostearate) and Gelucire 39/01 (semi-synthetic glycerides, i.e., C12-18 mono-, di- and tri-glycerides);
- Acetic, succinic, lactic, citric and/or tartaric esters of mono- and/or di-glycerides of fatty acids, for example, Myvacet 9-45 (distilled acetylated monoglycerides), Miglyol 829 (caprylic/capric diglyceryl succinate), Myverol SMG (mono/di-succinylated monoglycerides), Imwitor 370 (glyceryl stearate citrate), Imwitor 375 (glyceryl monostearate/citrate/lactate) and Crodatem T22 (diacetyl tartaric esters of monoglycerides);
- Propylene glycol mono- and/or di-esters of fatty acids, for example, Lauroglycol (propylene glycol monolaurate), Mirpyl (propylene glycol monomyristate), Captex 200 (propylene glycol dicaprylate/dicaprate), Miglyol 840 (propylene glycol dicaprylate/dicaprate) and Neobee M-20 (propylene glycol dicaprylate/dicaprate);
- Polyglycerol esters of fatty acids such as Plurol oleique (polyglyceryl oleate), Caprol ET (polyglyceryl mixed fatty acids) and Drewpol 10.10.10 (polyglyceryl oleate);
- Castor oil ethoxylates of low ethoxylate content (HLB<10) such as Etocas 5 (5 moles of ethylene oxide reacted with 1 mole of castor oil) and Sandoxylate 5 (5 moles of ethylene oxide reacted with 1 mole of castor oil;
- Acid and ester ethoxylates formed by reacting ethylene oxide with fatty acids or glycerol esters of fatty acids (HLB<10) such as Crodet 04 (polyoxyethylene (4) lauric acid), Cithrol 2 MS (polyoxyethylene (2) stearic acid), Marlosol 183 (polyoxyethylene (3) stearic acid) and Marlowet G12DO (glyceryl 12 EO dioleate). Sorbitan esters of fatty acids, for example, Span 20 (sorbitan monolaurate), Crill 1 (sorbitan monolaurate) and Crill 4 (sorbitan mono-oleate);
- Transesterification products of natural or hydrogenated vegetable oil triglyceride and a polyalkylene polyol (HLB<10), e.g. Labrafil M1944CS (polyoxyethylated apricot kernel oil), Labrafil M2125CS (polyoxyethylated corn oil) and Gelucire 37/06 (polyoxyethylated hydrogenated coconut);
- Alcohol ethyoxylates (HLB<10), e.g. Volpo N3 (polyoxyethylated (3) oleyl ether), Brij 93 (polyoxyethylated (2) oleyl ether), Marlowet LA4 (polyoxyethylated (4) lauryl ether); and
- Pluronics, for example, Polyoxyethylene-polyoxypropylene co-polymers and block co-polymers (HLB<10) e.g. Synperonic PE L42 (HLB=8) and Synperonic PE L61 (HLB-3)

The term "hydrophilic surfactant," as used herein is intended to mean a surfactant having an HLB of greater than 10, such as 10 to 45, for example, 10-15. In some embodiments, the hydrophilic surfactant is a polyoxyethylene sorbitan fatty acid ester, hydrogenated castor oil ethoxylate, PEG mono- and di-ester of palmitic and stearic acid, fatty acid ethoxylate, or combinations thereof. In some embodiments, the hydrophilic surfactant is selected from polyoxyethylene sorbitan fatty acid esters, hydrogenated castor oil ethoxylates, polyethylene glycol mono- and di-glycerol esters of caprylic, capric, palmitic and stearic acids, fatty acid ethoxylates, polyethylene glycol esters of alpha-tocopherol and its esters and combinations thereof. In some embodiments, the hydrophilic surfactant is a hydrogenated castor oil ethoxylate. In some embodiments, the hydrophilic surfactant is Cremophor RH 40 (polyoxyethyleneglycerol trihydroxystearate).

Provided is a method of treating conditions associated with a deficiency or absence of endogenous testosterone in a subject in need thereof comprising the steps of:

administering to the subject a defined dose of an oral pharmaceutical composition comprising testosterone undecanoate solubilized in a carrier comprising at least one lipophilic surfactant and at least one hydrophilic surfactant;

collecting a blood sample from the subject;

measuring the serum testosterone concentration in the subject; and increasing the dose of testosterone undecanoate when the measured serum testosterone concentration in the subject is less than about 425 ng/dL, decreasing the dose of testosterone undecanoate when the measured serum testosterone concentration in the subject is greater than about 970 ng/dL, or maintaining the dose of testosterone undecanoate when the measured serum testosterone concentration in the subject is between about 425 ng/dL and about 970 ng/dL.

Also provided is a method of treating chronic testosterone deficiency or its symptoms comprising the steps of:

administering daily to a subject in need thereof an oral pharmaceutical composition comprising 237 mg of testosterone undecanoate solubilized in a carrier comprising oleic acid, and polyoxyethyelene (40) hydrogenated castor oil, and optionally, borage seed oil and/or peppermint oil, twice a day, for a period of at least fourteen days;

collecting the subject's blood sample;

measuring the serum testosterone concentration in the subject five to seven hours following the daily administration of the oral pharmaceutical composition;

increasing the dose of testosterone equivalents administered daily to the subject by 50 mg when the serum testosterone concentration in the subject is less than 425 ng/dL, and decreasing the dose of testosterone equivalents administered daily to the subject by 25 mg when the serum testosterone concentration in the subject is greater than 970 ng/dL; and repeating until the serum testosterone concentration in the subject is between 425 and 970 ng/dL.

Also provided is a method of treating chronic testosterone deficiency in a subject in need thereof comprising the steps of:

administering daily to the subject a defined dose of an oral pharmaceutical composition comprising testosterone undecanoate solubilized in a carrier comprising at least one lipophilic surfactant and at least one hydrophilic surfactant;

measuring the circulating testosterone concentration in the subject from which blood is collected; and increasing the dose of testosterone undecanoate administered when the measured serum testosterone $C_6$ (i.e., serum T concentration in a blood sample drawn 6 hours post an oral TU dose) in the subject is less than about 425 ng/dL, decreasing each dose of testosterone undecanoate administered when the serum testosterone $C_6$ in the subject is greater than about 970 ng/dL, and maintaining each dose of testosterone undecanoate administered when the measured serum testosterone $C_6$ in the subject is between about 425 ng/dL and about 970 ng/dL.

Also provided is a method of treating chronic testosterone deficiency in a subject in need thereof comprising the steps of:

administering daily to the subject a defined dose of an oral pharmaceutical composition comprising testosterone undecanoate solubilized in a carrier comprising at least one lipophilic surfactant and at least one hydrophilic surfactant;

collecting the subject's blood sample;

measuring the serum testosterone concentration in the subject;

making a titration decision based on the measured serum testosterone concentration; and increasing the dose of testosterone undecanoate administered when the measured serum testosterone concentration in the subject is less than about 425 ng/dL, decreasing each dose of testosterone undecanoate administered when the measured serum testosterone concentration in the subject is greater than about 970 ng/dL, and maintaining each dose of testosterone undecanoate administered when the measured serum testosterone concentration in the subject is between about 425 ng/dL and about 970 ng/dL.

Also provided is a method of treating chronic testosterone deficiency in a subject in need thereof comprising the steps of:

administering to the subject a first dose of an oral pharmaceutical composition comprising a 237 mg dose of testosterone undecanoate (TU) solubilized in a carrier comprising at least one lipophilic surfactant and at least one hydrophilic surfactant;

after a first time period, measuring the subject's testosterone concentration; and increasing the dose of testosterone undecanoate administered when the measured serum testosterone concentration is less than about 425 ng/dL, decreasing the dose of testosterone undecanoate administered when the measured serum testosterone concentration is greater than about 970 ng/dL, and maintaining the dose of testosterone undecanoate administered when the measured serum testosterone concentration in the subject is between about 425 ng/dL and about 970 ng/dL.

Also provided is a method of treating chronic testosterone deficiency in a subject in need thereof comprising the steps of:

administering twice daily (BID) to the subject an oral pharmaceutical composition comprising a 237 mg dose of testosterone undecanoate (TU) solubilized in a carrier comprising at least one lipophilic surfactant and at least one hydrophilic surfactant;

collecting the subject's blood sample six hours after administration of the morning dose;

measuring the serum testosterone concentration in the subject 6 hours after the morning dose; and increasing the dose of testosterone undecanoate administered when the measured serum testosterone concentration in the subject is less than about 425 ng/dL, decreasing each dose of testosterone undecanoate administered when the measured serum testosterone concentration in the subject is greater than about 970 ng/dL, and maintaining each dose of testosterone undecanoate administered when the measured serum testosterone concentration in the subject is between about 425 ng/dL and about 970 ng/dL.

The present invention also provides methods of administering oral pharmaceutical formulations comprising testosterone esters that provide average steady state levels (concentrations) of testosterone, which fall within a desired "normal" or eugonadal range (i.e., about 300-1100 ng/dL) while avoiding the high $C_{max}$ values that are considered by the United States Food and Drug Administration to be undesirable. The patients whose $C_{avg}$ does not fall within the normal range for T can have $C_{avg}$ values either above or below the normal range, but the sum of both populations should not exceed 25%. FDA approval targets also state that less than 15% of treated subjects may have a $C_{max}$ value of 1500 ng/dL or greater, and that none may have a $C_{max}$ value exceeding 2500 ng/dL. Less than 5% of treated subjects may have a $C_{max}$ value falling in the range of 1800-2500 ng/dL.

Thus, also provided herein is a method of treating a population of humans suffering from chronic testosterone deficiency comprising the steps of:

a. administering daily to the subject a dose of an oral pharmaceutical composition comprising a testosterone ester solubilized in a carrier comprising at least one lipophilic surfactant and at least one hydrophilic surfactant;
b. collecting said subject's blood sample;
c. measuring the serum testosterone concentration in the subject; and
d. increasing the dose of testosterone ester administered in step a. when the measured serum testosterone concentration in the subject is less than about 425 ng/dL, decreasing each dose of testosterone ester administered in step a. when the measured serum testosterone concentration in the subject is greater than about 970 ng/dL, and maintaining each dose of testosterone ester administered in step a. when the measured serum testosterone concentration in the subject is between about 425 ng/dL and about 970 ng/dL, wherein, after treatment, the patients whose $C_{avg}$ does not fall within the normal range for T can have $C_{avg}$ values either above or below the normal range, but the sum of both populations should not exceed 25%. In other words, at least 75% of the population has a serum testosterone $C_{avg}$ within the normal range.

Also disclosed herein is a method of treating a population of humans suffering from chronic testosterone deficiency as described above wherein, after treatment, greater than 85% of the population has a $C_{max}$ below 1500 ng/dL, less than 15% of the population has a $C_{max}$ above 1500 ng/dL, less than 5% of the population has a $C_{max}$ above 1800 ng/dL, and 0% of the population has a $C_{max}$ above 2500 ng/dL.

In some embodiments, the steps are repeated until the serum testosterone concentration in the subject is between about 425 and about 970 ng/dL. In some embodiments, the steps are repeated until the serum testosterone concentration from blood collected 6 hours post-dose in the subject is between about 425 and about 970 ng/dL.

In some embodiments, the subject is diagnosed with hypogonadal conditions associated with structural or genetic etiologies. In some embodiments, the subject is diagnosed with primary hypogonadism. In some embodiments, the subject is diagnosed with testicular failure due to cryptorchidism, bilateral torsion, orchitis, vanishing testis syndrome, orchiectomy, Klinefelter syndrome, chemotherapy, or toxic damage from alcohol or heavy metals. In some embodiments, the subject is diagnosed with hypogonadotropic hypogonadism. In some embodiments, the subject is diagnosed with gonadotropin or luteinizing hormone-releasing hormone (LHRH) deficiency or pituitary-hypothalamic injury from tumors, trauma, or radiation. In some embodiments, the subject is not diagnosed with age-related hypogonadism.

In some embodiments, prior to administering the defined dose of an oral pharmaceutical composition, the method further comprises the step of confirming the diagnosis of hypogonadism. In some embodiments, the diagnosis of hypogonadism is confirmed if the serum testosterone concentrations measured on at least two separate days are below the normal range.

In some embodiments, the oral pharmaceutical composition is administered twice daily (BID). In some embodiments, the oral pharmaceutical composition is administered three times daily (TID). In some embodiments, the oral pharmaceutical composition is administered once daily (QD).

In some embodiments, the oral pharmaceutical composition comprises testosterone undecanoate and is administered twice daily (BID). In some embodiments, the oral pharmaceutical composition comprises testosterone undecanoate and is administered three times daily (TID).

In some embodiments, the oral pharmaceutical composition is administered in close proximity to a meal (e.g., immediately prior or after a meal, or 15 minutes prior to after a meal or 30 minutes prior to or after a meal) wherein the meal contains at least about 15 g of fat.

In some embodiments, the meal contains at least about 30 g of fat.

In some embodiments, the meal contains at least about 45 g of fat.

In some embodiments, blood is drawn 4-8 hours (i.e., $C_{4-8}$) after administration of the dose. In some embodiments, blood is drawn 5-7 hours after administration of the dose. In some embodiments, blood is drawn 6 hours after administration of v dose.

In some embodiments, blood is drawn at least 7 days after starting treatment. In some embodiments, blood is drawn at least 7 days following dose adjustment.

In some embodiments, the subject's testosterone concentration is measured after a first time period. In some embodiments, the first period is chosen from 1, 2, 3, 4, 5, 6, 7, and 8 hours. In some embodiments, the first period is 4-8 hours. In some embodiments, the first period is 5-7 hours. In some embodiments, the first period is 6 hours.

In some embodiments, the plasma testosterone concentration is measured five to seven hours following the daily administration of the oral pharmaceutical composition. In some embodiments, the testosterone concentration is measured in serum from a blood sample collected in a plain tube drawn 5-7 hours after the morning dose. In some embodiments, the testosterone concentration is measured in serum from a blood sample collected in a plain tube drawn 5-7 hours after at least 7 days after starting treatment. In some embodiments, the testosterone concentration is measured in serum from a blood sample collected in a plain tube drawn 5-7 hours following dose adjustment.

In some embodiments, the serum testosterone $C_{avg}$ is estimated on the basis of a single blood sample (i.e., $C_6$ serum T concentration). In some embodiments, the serum testosterone $C_{avg}$ is estimated on the basis of a single blood sample collected 4 to 8 hours after administering the oral pharmaceutical composition. In some embodiments, the serum testosterone $C_{avg}$ is estimated on the basis of a single blood sample collected 5 to 7 hours after administering the oral pharmaceutical composition. In some embodiments, the serum testosterone concentration at 6 hours after administration of the morning dose is used to approximate $C_{avg}$. In some embodiments, the serum testosterone $C_{avg}$ is estimated on the basis of a single blood sample collected 6 hours after administering the oral pharmaceutical composition.

In some embodiments, the serum testosterone $C_{avg}$ determined based on the measurement of testosterone via an immunometric assay, or a liquid chromatography tandem mass spectrometry (LC-MS/MS) assay.

In some embodiments, the steady-state serum testosterone $C_{avg}$ is estimated based on the measurement of testosterone in a single blood sample collected about 4 to 8 hours after oral testosterone dose after at least seven days of daily treatment with the oral pharmaceutical composition. In some embodiments, the steady-state serum testosterone $C_{avg}$ is estimated based on the measurement of testosterone in a single blood sample collected about 5 to 7 hours after oral testosterone dose after at least seven days of daily treatment with the oral pharmaceutical composition. In some embodiments, the steady-state serum testosterone $C_{avg}$ is estimated based on the measurement of T in a single blood sample collected about 6 hours after oral testosterone dose after at least seven days of daily treatment with the oral pharmaceutical composition.

In some embodiments, the serum testosterone $C_{avg}$ is determined after at least 10 to 14 days of daily treatment with the oral pharmaceutical composition. In some embodiments, the serum testosterone $C_{avg}$ is determined after at least 30 days of daily treatment with the oral pharmaceutical composition.

In some embodiments, the circulating testosterone concentration is measured in serum. In some embodiments, the serum testosterone concentration is measured four to eight hours after administering the oral pharmaceutical composition.

Also provided is a method of measuring a subject's testosterone concentration comprising: collecting the subject's blood sample and obtaining the serum from the blood sample; measuring the subject's serum testosterone concentration; and estimating the subject's blood testosterone concentration by measuring the subject's serum testosterone concentration and dividing that concentration by a conversion factor.

In some embodiments, measuring the subject's testosterone concentration comprises collecting the subject's blood sample and obtaining the serum from the blood sample. In some embodiments, measuring the subject's testosterone concentration is comprises measuring the subject's serum testosterone concentration. In some embodiments, measuring the subject's testosterone concentration comprises estimating the subject's blood testosterone concentration by measuring the subject's serum testosterone concentration and dividing that concentration by a conversion factor.

In some embodiments, the conversion factor is between about 1.0 and about 1.4. In some embodiments, the conversion factor is between about 1.032 and about 1.396.

In some embodiments, the conversion factor is 1.214. In some embodiments, if the sample is a serum sample, then dividing the T concentration measured in serum by 1.214 would yield the expected T concentration in NaF-EDTA plasma.

In some embodiments, the incidence of concordant titration decisions is approximately 99%.

In some embodiments, concordant titration decisions reflect an on-diagonal concordance of 75% and 63% and an effective off-diagonal titration decision of 24% and 36%.

In some embodiments, the defined dose is about 237 mg of testosterone undecanoate, administered twice daily.

In some embodiments, the 237 mg dose of testosterone undecanoate is increased to 316 mg, administered twice daily, when the measured serum testosterone concentration in the subject is less than about 425 ng/dL and the dose of testosterone undecanoate is decreased to 198 mg, administered twice daily, when the measured serum testosterone concentration in the subject is greater than about 970 ng/dL.

In some embodiments, the defined dose is about 316 mg of testosterone undecanoate, administered twice daily. In some embodiments, the defined dose is about 316 mg of testosterone undecanoate, administered twice daily and the dose of testosterone undecanoate is increased to 396 mg, administered twice daily, when the measured serum testosterone concentration in the subject is less than about 425 ng/dL; and the dose of testosterone undecanoate is decreased to 237 mg, administered twice daily, when the measured serum testosterone concentration in the subject is greater than about 970 ng/dL.

In some embodiments, the defined dose is about 198 mg of testosterone undecanoate, administered twice daily. In some embodiments, the defined dose is about 198 mg of testosterone undecanoate, administered twice daily and the dose of testosterone undecanoate is increased to 237 mg, administered twice daily, when the measured serum testosterone concentration in the subject is less than about 425 ng/dL; and the dose of testosterone undecanoate is decreased to 158 mg, administered twice daily, when the measured serum testosterone concentration in the subject is greater than about 970 ng/dL.

In some embodiments, the defined dose is about 396 mg of testosterone undecanoate, administered twice daily. In some embodiments, the defined dose is about 396 mg of testosterone undecanoate, administered twice daily and the dose of testosterone undecanoate is decreased to 316 mg, administered twice daily, when the measured serum testosterone concentration in the subject is greater than about 970 ng/dL.

In some embodiments, the defined dose is about 158 mg of testosterone undecanoate, administered twice daily. In some embodiments, the defined dose is about 158 mg of testosterone undecanoate, administered twice daily and the dose of testosterone undecanoate is increased to 198 mg, administered twice daily, when the measured serum testosterone concentration in the subject is less than about 425 ng/dL; and treatment is discontinued when the subject's measured serum testosterone concentration in the subject is greater than about 970 ng/dL.

In some embodiments, the dose adjustment scheme is as shown in Table 1.

TABLE 1

| Testosterone Concentration in Serum From Plain (Red-Top) Tube Drawn 6 hours After Dose | Current Dose (mg, BID) | New Dose (mg, BID) |
|---|---|---|
| <425 ng/dL | 158 | 198 |
| | 198 | 237 |
| | 237 | 316 |
| | 316 | 398 |
| 425-970 ng/dL | No Dose Change | |
| >970 ng/dL | 396 | 316 |
| | 316 | 237 |
| | 237 | 198 |
| | 198 | 158 |
| | 158 | Discontinue Treatment |

In some embodiments, the initial dose of testosterone undecanoate in the oral pharmaceutical composition is equivalent to about 150 mg of testosterone. In some embodiments, the oral pharmaceutical composition comprises testosterone undecanoate. In some embodiments, the oral pharmaceutical composition administered comprises about 237 mg of testosterone undecanoate that equates to 150 mg of testosterone.

In some embodiments, the initial dose of testosterone undecanoate in the oral pharmaceutical composition is equivalent to about 200 mg of testosterone per dose. In some embodiments, the oral pharmaceutical composition comprises testosterone undecanoate. In some embodiments, the oral pharmaceutical composition administered comprises about 316 mg of testosterone undecanoate that equates to 200 mg testosterone per dose.

In some embodiments, the initial dose of testosterone undecanoate in the oral pharmaceutical composition is equivalent to about 250 mg of testosterone per dose. In some embodiments, the oral pharmaceutical composition comprises testosterone undecanoate. In some embodiments, the oral pharmaceutical composition administered comprises about 396 mg of testosterone undecanoate that equates to 250 mg testosterone per dose.

In some embodiments, the initial dose of testosterone undecanoate in the oral pharmaceutical composition is equivalent to about 125 mg of testosterone per dose. In some embodiments, the oral pharmaceutical composition comprises testosterone undecanoate. In some embodiments, the oral pharmaceutical composition administered comprises about 198 mg of testosterone undecanoate that equates to 125 mg testosterone per dose.

In some embodiments, the initial dose of testosterone undecanoate in the oral pharmaceutical composition is equivalent to about 100 mg of testosterone per dose. In some embodiments, the oral pharmaceutical composition comprises testosterone undecanoate. In some embodiments, the oral pharmaceutical composition administered comprises about 158 mg of testosterone undecanoate that equates to 100 mg testosterone per dose.

In some embodiments, the dose of testosterone undecanoate in the administered oral pharmaceutical composition is increased by the equivalent of about 25 to about 75 mg of testosterone when the serum testosterone $C_6$ in the subject is less than about 425 ng/dL, and decreased by the equivalent of about 10 to about 75 mg of testosterone when the serum testosterone $C_6$ in the subject is greater than about 970 ng/dL.

In some embodiments, the dose of testosterone undecanoate in the administered oral pharmaceutical composition is increased by the equivalent of about 40 to about 60 mg of testosterone when the serum testosterone $C_6$ in the subject is less than about 425 ng/dL.

In some embodiments, the dose of testosterone undecanoate in the administered oral pharmaceutical composition is increased by the equivalent of about 50 mg of testosterone when the serum testosterone $C_6$ in the subject is less than about 425 ng/dL.

In some embodiments, the dose of testosterone undecanoate in the administered oral pharmaceutical composition is decreased by the equivalent of about 10 to about 60 mg of testosterone when the serum testosterone $C_6$ in the subject is greater than about 970 ng/dL.

In some embodiments, the dose of testosterone undecanoate in the administered oral pharmaceutical composition is decreased by the equivalent of about 25 to about 50 mg of testosterone when the serum testosterone $C_6$ in the subject is greater than about 970 ng/dL.

In some embodiments, the dose of testosterone undecanoate in the administered oral pharmaceutical composition is decreased by the equivalent of about 25 mg of testosterone when the serum testosterone $C_6$ in the subject is greater than about 970 ng/dL.

In some embodiments, the dose of oral pharmaceutical composition is titrated after 21 days of daily treatment. In some embodiments, the dose of oral pharmaceutical composition is titrated after 56 days of daily treatment. In some embodiments, the dose of oral pharmaceutical composition is titrated after 105 days of daily treatment.

In some embodiments, the dose of oral pharmaceutical composition is titrated after at least 30 days of daily treatment. In some embodiments, the dose of oral pharmaceutical composition is titrated after 35 days of daily treatment. In some embodiments, the dose of oral pharmaceutical composition is titrated after at least 60 days of daily treatment. In some embodiments, the dose of oral pharmaceutical composition is titrated after 70 days of daily treatment.

In some embodiments, the oral pharmaceutical composition comprises testosterone undecanoate solubilized in a carrier comprising at least one lipophilic surfactant and at least one hydrophilic surfactant in a total lipophilic surfactant to total hydrophilic surfactant ratio (w/w) falling in the range of about 6:1 to 3.5:1, which composition, upon once- or twice-daily oral administration, provides an average serum testosterone concentration at steady state falling in the range of about 425 to about 970 ng/dL.

In some embodiments, the composition comprises 15-30% (w/w) of testosterone undecanoate.

In some embodiments, the composition comprises 15-20% (w/w) of testosterone undecanoate.

In some embodiments, the composition comprises 18-22% (w/w) of testosterone undecanoate. In some embodiments, the oral pharmaceutical composition comprises about 18 to 22 percent by weight of a solubilized testosterone undecanoate.

In some embodiments, the composition comprises 25-30% (w/w) of testosterone undecanoate.

In some embodiments, the oral pharmaceutical composition comprises about 10-20 percent by weight of solubilized testosterone undecanoate, about 5-20 percent by weight of hydrophilic surfactant, about 50-70 percent by weight of lipophilic surfactant; and about 10-15 percent by weight of digestible oil, wherein the oral pharmaceutical composition is free of ethanol.

In some embodiments, oral pharmaceutical compositions comprise testosterone undecanoate solubilized in a carrier in a lipophilic surfactant and a hydrophilic surfactant. The compositions are designed to be self-emulsifying drug delivery systems (SEDDS) and iterations thereof such as self-microemulsified drug delivery systems (SMEDDS) and self-nanoemulsified drug delivery systems (SNEDDS) so that a testosterone undecanoate-containing emulsion, microemulsion, nanoemulsion (or dispersion) is formed upon mixing with intestinal fluids in the gastrointestinal tract.

In some embodiments, the oral pharmaceutical composition comprises 15 to 17 percent by weight of the at least one hydrophilic surfactant.

In some embodiments, the oral pharmaceutical composition comprises 50 to 55 percent by weight of the at least one lipophilic surfactant.

In some embodiments, the oral pharmaceutical composition further includes digestible oil. A digestible oil is defined herein as an oil that is capable of undergoing de-esterification or hydrolysis in the presence of pancreatic lipase in vivo under normal physiological conditions. Specifically, digestible oils may be complete glycerol triesters of medium chain ($C_7$-$C_{13}$) or long chain ($C_{14}$-$C_{22}$) fatty acids with low molecular weight (up to $C_6$) mono-, di- or polyhydric alcohols. Some examples of digestible oils for use the oral pharmaceutical composition include: vegetable oils (e.g., soybean oil, safflower seed oil, corn oil, olive oil, castor oil, cottonseed oil, arachis oil, sunflower seed oil, coconut oil, palm oil, rapeseed oil, black currant oil, evening primrose oil, grape seed oil, wheat germ oil, sesame oil, avocado oil, almond, borage, peppermint and apricot kernel oils) and animal oils (e.g., fish liver oil, shark oil and mink oil). In some embodiments, the digestible oil is a vegetable oil. In some embodiments, the vegetable oil is soybean oil, safflower seed oil, corn oil, olive oil, castor oil, cottonseed oil, arachis oil, sunflower seed oil, coconut oil, palm oil, rapeseed oil, evening primrose oil, grape seed oil, wheat germ oil, sesame oil, avocado oil, almond oil, borage oil, peppermint oil, apricot kernel oil, or combinations thereof. Particular digestible oils are those with high gamma-linolenic acid (GLA) content such as, black currant oil, primrose oil and borage oil, as well as any other digestible oil that can be enriched in GLA acid through enzymatic processes.

In some embodiments, methods and compositions for modulating (i.e., sustaining) the rate of available serum testosterone by incorporating component(s) that may biochemically modulate (1) testosterone ester absorption, (2) testosterone ester metabolism to testosterone, and/or (3) metabolism of testosterone to dihydrotestosterone (DHT). For example, the inclusion of medium to long chain fatty acid esters can enhance testosterone ester absorption. In this way, more testosterone ester may stave off hydrolysis in the gut and enter the blood stream. In other words, the fatty acid ester may competitively inhibit esterases that would otherwise metabolize the testosterone ester. Examples of other esters or combinations thereof include botanical extracts or benign esters used as food additives (e.g., propylparaben, octylacetate and ethylacetate).

Other components that can modulate testosterone ester absorption include "natural" and synthetic inhibitors of 5a-reductase, which is an enzyme present in enterocytes and other tissues that catalyzes the conversion of T to DHT. Complete or partial inhibition of this conversion may both increase and sustain increased plasma levels of T after oral dosing with testosterone ester while concomitantly reducing plasma DHT levels. Borage oil, which contains a significant amount of the 5a-reductase inhibitor, gamma-linolenic acid (GLA), is an example of a "natural" modulator of testosterone ester metabolism. Other than within borage oil, of course, GLA could be added directly as a separate component. Furthermore, any digestible oil as listed above can be enzymatically enriched in GLA. Many natural inhibitors of 5a-reductase are known in the art (e.g., epigallocatechin gallate, a catechin derived primarily from green tea and saw palmetto extract from berries of the Serenoa repens species, phytosterols and lycopene), all of which may be suitable in the compositions described herein. Non-limiting examples of synthetic 5a-reductase inhibitors include compounds such as finasteride, dutasteride and the like.

In some embodiments, the oral pharmaceutical composition further includes one or more additional therapeutic agents. In some embodiments, the agent is a second testosterone ester, a synthetic progestin, an inhibitor of type-I and/or type II 5a-reductase, an inhibitor of CYP3A4, finasteride, dutasteride, thiazide diuretics, and calcium channel blockers, or combinations thereof. In some embodiments, the agent is borage oil. In some embodiments, the agent is peppermint oil and related substances such as menthol and menthol esters. In some embodiments, the agent is a second testosterone ester.

In some embodiments, the thiazide diuretic is selected from chlorothiazide, chlorthalidone, indapamide, hydrochlorothiazide, methyclothiazide, and metolazone.

In some embodiments, the calcium channel blocker is selected from Amlodipine, Diltiazem, Felodipine, Isradipine, Nicardipine, Nifedipine, Nisoldipine, and Verapamil.

Optional cosolvents suitable with the oral pharmaceutical composition are, for example, water, short chain mono-, di-, and polyhydric alcohols, such as ethanol, benzyl alcohol, glycerol, propylene glycol, propylene carbonate, polyethylene glycol (PEG) with an average molecular weight of about 200 to about 10,000, diethylene glycol monoethyl ether (e.g., Transcutol HP), and combinations thereof. In particular, such cosolvents, especially monohydric alcohols, are excluded altogether. Thus, in some embodiments, the oral pharmaceutical compositions are free of monohydric alcohols. In some embodiments, the monohydric alcohols are $C_2$-$C_{18}$ aliphatic or aromatic alcohols. In some embodiments, the compositions are free of ethyl or benzyl alcohols.

In some embodiments, the compositions contain between 0% and 10% (w/w) of polyethylene glycol with an average molecular weight of about 8,000 (PEG-8000). In some embodiments, the compositions contain between 5% and 10% (w/w) of PEG-8000.

In some embodiments, the oral pharmaceutical composition is a liquid, semi-solid or solid dosage form. In some embodiments, the oral pharmaceutical compositions are liquid or semi-solid at ambient temperatures. Furthermore, these pharmaceutical compositions can be transformed into solid dosage forms through adsorption onto solid carrier particles, such as silicon dioxide, calcium silicate or magnesium aluminometasilicate to obtain free-flowing powders that can be either filled into hard capsules or compressed into tablets. Hence, the term "solubilized" herein, should be interpreted to describe an active pharmaceutical ingredient (API), which is dissolved in a liquid solution or which is uniformly dispersed in a solid carrier. In addition, sachet type dosage forms can be formed and used. In some embodiments, the oral pharmaceutical composition is filled into a hard or soft gelatin capsule.

In some embodiments, the oral pharmaceutical composition comprises: about 15-20 percent by weight of solubilized testosterone undecanoate, about 5-20 percent by weight of hydrophilic surfactant, about 50-70 percent by weight of lipophilic surfactant; and about 1-10 percent by weight of polyethylene glycol 8000. In some embodiments, the oral pharmaceutical composition comprises about 15 percent by weight of testosterone undecanoate, about 63 percent by weight of glyceryl mono-linoleate, about 16 percent by weight of polyoxyethylene (40) hydrogenated castor oil, and about 6 percent by weight of polyethylene glycol having a molecular weight of about 8000 g/mol (PEG 8000).

The compositions details of Table 2 (mg/capsule and wt. percentage) are based on an approximate fill weight of 800 mg fill weight per '00' hard gelatin capsule. However, at testosterone undecanoate amounts less than about 100 mg/capsule, the formulations may be proportionally adjusted for smaller total fill weights that would permit use of smaller hard gelatin capsules (e.g., size '0' or smaller size if needed).

As well, it should be apparent to one of ordinary skill in the art that many, if not all, of the surfactants within a category (e.g., lipophilic, hydrophilic, etc.) may be exchanged with another surfactant from the same category. Thus, while many of the formulations comprise oleic acid, one of ordinary skill in the art should recognize other lipophilic surfactants (e.g., those listed above) may be suitable as well. Similarly, while Table 2 lists formulations comprising Cremophor RH40 (HLB=13), one of ordinary skill in the art should recognize other hydrophilic surfactants (e.g., those listed above) may be suitable. Borage oil, peppermint oil, BHT, and ascorbyl palmitate may be substituted for chemically similar substances or eliminated.

TABLE 2

| | Composition % w/w (mg/ "00" capsule)[1] | | | | | | | Fill |
|---|---|---|---|---|---|---|---|---|
| F. | TU | Oleic Acid | Cremophor RH40 | Borage Oil | Peppermint Oil | BHT | Ascorbyl Palmitate | Wt. (mg)[2] |
| 1 | 20 | 51.5 | 16 | 10 | 2.5 | 0.06 | — | 800 |
| | (158) | (413) | (128.5) | (80) | (20) | (0.5) | | |
| 2 | 15 | 54.5 | 18 | 10 | 2.5 | 0.02 | 0.8 | 806.6 |
| | (120) | (436) | (144) | (80) | (20) | (0.2) | (6.4) | |
| 3 | 17 | 52.5 | 18 | 10 | 2.5 | 0.02 | 0.8 | 806.6 |
| | (136) | (420) | (144) | (80) | (20) | (0.2) | (6.4) | |
| 4 | 19 | 50.5 | 18 | 10 | 2.5 | 0.02 | 0.8 | 806.6 |
| | (152) | (404) | (144) | (80) | (20) | (0.2) | (6.4) | |
| 5 | 21 | 50 | 16.5 | 10 | 2.5 | 0.02 | 0.8 | 806.6 |
| | (168) | (400) | (132) | (80) | (20) | (0.2) | (6.4) | |
| 6 | 23 | 50 | 14.5 | 10 | 2.5 | 0.02 | 0.8 | 806.6 |
| | (184) | (400) | (116) | (80) | (20) | (0.2) | (6.4) | |
| 7 | 25 | 50 | 12.5 | 10 | 2.5 | 0.02 | 0.8 | 806.6 |
| | (200) | (400) | (100) | (80) | (20) | (0.2) | (6.4) | |
| 8 | 16 | 53.5 | 18 | 10 | 2.5 | 0.02 | 0.8 | 806.6 |
| | (128) | (428) | (144) | (80) | (20) | (0.2) | (6.4) | |
| 9 | 18 | 51.5 | 18 | 10 | 2.5 | 0.02 | 0.8 | 806.6 |
| | (144) | (413) | (144) | (80) | (20) | (0.2) | (6.4) | |
| 10 | 22 | 50 | 15.5 | 10 | 2.5 | 0.02 | 0.8 | 806.6 |
| | (176) | (400) | (124 | (80) | (20) | (0.2) | (6.4) | |
| 11 | 24 | 50 | 13.5 | 10 | 2.5 | 0.02 | 0.8 | 806.6 |
| | (192) | (400) | (108) | (80) | (20) | (0.2) | (6.4) | |
| 12 | 15 | 55.5 | 17 | 10 | 2.5 | 0.02 | 0.8 | 806.6 |
| | (120) | (444) | (136) | (80) | (20) | (0.2) | (6.4) | |
| 13 | 17 | 53.5 | 17 | 10 | 2.5 | 0.02 | 0.8 | 806.6 |
| | (136) | (428) | (136) | (80) | (20) | (0.2) | (6.4) | |
| 14 | 19 | 51.5 | 17 | 10 | 2.5 | 0.02 | 0.8 | 806.6 |
| | (152) | (412) | (136) | (80) | (20) | (0.2) | (6.4) | |
| 15 | 15 | 56.5 | 16 | 10 | 2.5 | 0.02 | 0.8 | 806.6 |
| | (120) | (452) | (128) | (80) | (20) | (0.2) | (6.4) | |
| 16 | 17 | 54.5 | 16 | 10 | 2.5 | 0.02 | 0.8 | 806.6 |
| | (136) | (436) | (128) | (80) | (20) | (0.2) | (6.4) | |
| 17 | 19 | 52.5 | 16 | 10 | 2.5 | 0.02 | 0.8 | 806.6 |
| | (152) | (420) | (128) | (80) | (20) | (0.2) | (6.4) | |
| 18 | 21 | 50.5 | 16 | 10 | 2.5 | 0.02 | 0.8 | 806.6 |
| | (168) | (404) | (128) | (80) | (20) | (0.2) | (6.4) | |
| 19 | 20 | 50.5 | 17 | 10 | 2.5 | 0.02 | 0.8 | 806.6 |
| | (160) | (404) | (136) | (80) | (20) | (0.2) | (6.4) | |
| 20 | 20 | 51.5 | 16 | 10 | 2.5 | 0.02 | 0.8 | 806.6 |
| | (160) | (412) | (128) | (80) | (20) | (0.2) | (6.4) | |
| 21 | 15 | 57.5 | 15 | 10 | 2.5 | 0.02 | 0.8 | 806.6 |
| | (120) | (460) | (120) | (80) | (20) | (0.2) | (6.4) | |
| 22 | 16 | 56.5 | 15 | 10 | 2.5 | 0.02 | 0.8 | 806.6 |
| | (128) | (452) | (120) | (80) | (20) | (0.2) | (6.4) | |
| 23 | 17 | 55.5 | 15 | 10 | 2.5 | 0.02 | 0.8 | 806.6 |
| | (136) | (444) | (120) | (80) | (20) | (0.2) | (6.4) | |
| 24 | 18 | (54.5 | 15 | 10 | 2.5 | 0.02 | 0.8 | 806.6 |
| | (144) | (436) | (120) | (80) | (20) | (0.2) | (6.4) | |
| 25 | 19 | 53.5 | 15 | 10 | 2.5 | 0.02 | 0.8 | 806.6 |
| | (152) | (428) | (120) | (80) | (20) | (0.2) | (6.4) | |
| 26 | 20 | 51.5 | 16 | 9.4 | 3.1 | 0.06 | — | 800 |
| | (158) | (413) | (128.5) | (75) | (25) | (0.5) | | |
| 27 | 20 | 51.5 | 16 | 10.6 | 1.9 | 0.06 | — | 800 |
| | (158) | (413) | (128.5) | (85) | (15) | (0.5) | — | |
| 28 | 20 | 51.5 | 16 | 11.2 | 1.2 | 0.02 | 0.8 | 806.1 |
| | (158) | (413) | (128.5) | (90) | (10) | (0.2) | (6.4) | |
| 29 | 20 | 51.5 | 16 | 11.8 | 0.6 | 0.02 | 0.8 | 806.1 |
| | (158) | (413) | (128.5 | (95) | (5) | (0.2) | (6.4) | |
| 30 | 25 | 50 | 12.5 | 10.6 | 1.9 | 0.06 | — | 800.5 |
| | (200) | (400) | (100) | (85) | (15) | (0.5) | | |

[1]Milligram weights rounded to nearest whole number; 800 (±10%)

[2]±8 mg

In some embodiments, the oral pharmaceutical composition comprises about 19.8 percent by weight of solubilized testosterone undecanoate, about 51.6 percent by weight of oleic acid, about 16.1 percent by weight of polyoxyethylene (40) hydrogenated castor oil, about 10 percent by weight of borage seed oil, about 2.5 percent by weight of peppermint oil, and about 0.03 percent by weight of butylated hydroxytoluene (BHT).

Particular formulations of TU filled into size "00" capsules are:

| Formulation A | | |
|---|---|---|
| Ingredients | mg/capsule | %, w/w |
| Testosterone Undecanoate | 158.3 | 19.8 |
| Oleic Acid | 413.1 | 51.6 |
| Cremophor RH 40 | 128.4 | 16.1 |
| Borage Seed Oil | 80.0 | 10 |
| Peppermint Oil | 20.0 | 2.5 |
| BHT | 0.2 | 0.03 |
| Total | 800 | 100 |

| Formulation B | | |
|---|---|---|
| Ingredients | mg/capsule | %, w/w |
| Testosterone Undecanoate | 158.3 | 19.8 |
| Oleic Acid | 412.5 | 51.6 |
| Cremophor RH 40 | 128.4 | 16.0 |
| Peppermint Oil | 20.0 | 2.5 |
| Borage Seed Oil + 0.03% BHT | 80.0 | 10 |
| Ascorbyl Palmitate | 0.8 | 0.1 |
| Total | 800 | 100 |

| Formulation C | | |
|---|---|---|
| Ingredients | mg/capsule | %, w/w |
| Testosterone Undecanoate | 120 | 15 |
| Cremophor RH 40 | 128 | 16 |
| Maisine 35-1 | 504 | 63 |
| Polyethylene Glycol 8000 | 48 | 6 |
| TOTAL | 800 | 100 |

In some embodiments, the oral pharmaceutical composition comprises about 19.8 percent by weight of solubilized testosterone undecanoate, about 51.6 percent by weight of oleic acid, and about 16.1 percent by weight of polyoxyethylene (40) hydrogenated castor oil. In some embodiments, the oral pharmaceutical composition further comprises about 10 percent by weight of borage seed oil and about 2.5 percent by weight of peppermint oil. In some embodiments, the oral pharmaceutical composition comprises about 15 percent by weight of solubilized testosterone undecanoate; about 16 percent by weight of polyoxyethylene (40) hydrogenated castor oil; about 63 percent by weight of glyceryl monolinoleate; and about 6 percent by weight In some embodiments, the oral pharmaceutical composition exhibits a percent (%) in vitro dissolution profile in 5% Triton X-100 solution in phosphate buffer, pH 6.8, indicating release from the composition of substantially all of the solubilized testosterone undecanoate within about 2 hours.

In some embodiments, the oral pharmaceutical composition exhibits a percent (%) in vitro dissolution profile in 5% Triton X-100 solution in phosphate buffer, pH 6.8, indicating release from the composition of substantially all of the solubilized testosterone undecanoate within about 1 hour.

EXAMPLES

Baseline T Concentrations

Baseline concentrations of T were determined prior to the start of the study and immediately prior to the start of each treatment cycle (i.e., after each 7 to 14-day washout period). The washout periods were sufficiently long to assure that T concentrations from the previous dosing cycle were no longer detectable.

Example—Influence of Blood Collection Tubes

Testosterone undecanoate is metabolized into testosterone. Its degradation in whole blood into testosterone has been studied in conditions typically used in clinical trials. It was observed that TU degrades extensively to testosterone in human blood under conditions typical of harvesting serum, causing overestimation of testosterone concentration.

Historically, most testosterone monitoring for diagnostic purposes and for testosterone replacement therapy (TRT) dose titration has been based on the testosterone concentration in blood concentrations in tubes without additives. However, many of the FDA approved immunoassays can accurately measure testosterone in serum as well as EDTA-plasma, or heparin-plasma. For subjects receiving oral testosterone undecanoate (TU), it has been proposed that monitoring of blood concentrations should be done with tubes that contain a nonspecific esterase inhibitor, sodium fluoride (NaF). Collecting the blood samples in tubes containing NaF may influence the blood testosterone concentration. Namely, use of NaF when oral TU is administered will enable a more accurate assay of true circulating T concentration.

As previously noted, despite the inaccuracy of measuring testosterone in serum in men treated with oral testosterone esters, specifically with oral TU, the desirability of the serum matrix and blood handling requirements for immunoassays for testosterone still make serum a desirable medium for measurement of testosterone. Collecting samples in NaF-EDTA tubes which are processed on ice is not convenient in the clinical setting and the plasma is not a validated matrix for immunoassays; however, measuring the T in this plasma allows for accurate measurements of T which are necessary in clinical trials, such as those required by regulatory agencies. It is therefore necessary to develop a method of deriving a way to correlate a serum testosterone levels (plain tube collected and allowed to clot for 30 minutes before centrifugation to collect serum) with a T level measured in NaF-EDTA plasma level (NaF-EDTA tube collected and allowed to sit for 30 minutes on ice before centrifugation to collect plasma).

Each study participant has blood drawn and the study drug (comprising 396 mg TU) is dispensed, followed by administration of the first study drug dose immediately prior to a breakfast meal containing 30 g fat. Prior to discharge from the clinical facility, the subjects will be instructed to take 396 mg TU by mouth immediately prior to their dinner meal on Day 1, then twice daily on Days 2-6 immediately prior to their breakfast and dinner meals, and on Day 7 in the morning, immediately prior to their breakfast meal.

Subjects will return to the Clinic on Day 7 in the late afternoon (before dinner) with their study medication. Upon arrival at the clinic, their study drug will be counted to determine compliance during Day 1 through Day 7 post-AM dose. They will then be administered the study drug 396 mg TU by mouth immediately prior to a dinner meal (containing 30 g fat) which will be provided. Subjects will be instructed to consume the dinner in approximately 20 minutes. Subjects will remain in the unit overnight.

On the $8^{th}$ day, 5 hrs after their AM meal, blood is collected in plain, EDTA and NaF-EDTA tubes. The plain tubes sit at room temperature (RT). The EDTA and NaF-EDTA tubes are placed on ice. The blood is spun (centrifuged) at various intervals after it is drawn (0, 15, 30, 60, 90 and 120 minutes, except plain which do not have a 0- and 15-minute sample).

Samples will be collected into multiple Plain, EDTA and NaF-EDTA tubes. The Plain tube will be incubated at RT to allow blood clotting, as recommended by Clinical and Laboratory Standards Institute (CLSI 2010). EDTA and NaF-EDTA tubes will be held on ice. After a defined period (between zero and 120 minutes), the tube(s) will be centrifuged and the serum/plasma transferred into freezer vial/tube(s) and frozen. The study site was given specific instructions on sample handling. The handling instructions were specific to the sample collection tube type and are presented in the following paragraphs.

Plain Collection Tube—Incubated at room temperature (serum): Collected blood tubes are labelled with the incubation time points listed described above and are incubated at room temperature for a minimum of 30 minutes. Centrifugation earlier than 30 minutes is not appropriate since the blood will not be fully clotted. Each sample will be centrifuged at the specified time point for 20 minutes at >1000 g. For each blood collection tube, serum will be separated promptly after centrifugation and transferred into appropriately-labelled polypropylene tubes. The serum samples will then be stored at −20 °C (+5 °C) prior to analysis.

NaF-EDTA Tubes—Incubated in ice bath (plasma): Collected blood tubes are labelled with the incubation time points listed described above and incubated in an ice bath for the specified incubation time points and then centrifuged for 20 minutes at >1000 g. For each blood collection tube, plasma will be separated promptly after centrifugation and transferred into appropriately-labelled polypropylene tubes. The plasma samples will then be stored at −20 °C (±5 °C) prior to analysis.

The concentration of total T and TU will be determined in the serum/plasma samples of all subjects using validated LC/MS/MS methods at Syneos Health Laboratories located in Quebec City, Quebec, Canada. The analytical procedures will be conducted in compliance with the laboratory's Standard Operating Procedures.

In order to calculate the ex vivo increase in T concentrations due to TU to T conversion, it is necessary to know the initial T concentration (e.g., T concentration in circulation). When calculating the ex vivo TU to T conversion in experiments where TU is spiked into blood, the unspiked blood's T concentration serves as the true baseline. When TU to T conversion is calculated in experiments where oral TU is administered, then the closest approximation to the "true" baseline value is the T concentration in a blood sample which is processed immediately after phlebotomy (e.g., centrifuged at time=0). Since samples in Plain tubes need 30 minutes to clot, it is not possible to get a "true" baseline value for serum. Therefore, as a surrogate for a serum "true" baseline, the Day 8 EDTA "true" baseline (time=0) will be used.

One of the goals of this study was to determine whether the T concentration in blood samples collected into Plain tubes (yielding serum) can be used for making dose titration decisions. In previous studies, dose titration decisions were based on T concentrations in NaF-EDTA plasma. Dose titration decisions were based on a 24 hr $C_{avg}$, but concordance analysis demonstrated that a sample collected about six hours post-morning dose can approximate the patient's $C_{avg}$ and thus effectively guide dose titration.

When comparing the T concentration measured in NaF-EDTA tubes with that in Plain tubes, it is necessary to consider 2 factors. These 2 factors are the effect that NaF has on T levels and the effect of post-collection TU to T conversion has on T levels.

First, NaF negatively impacts the measurement of T concentrations (Wang 2008, Lachance 2015, Ceponis 2018) by LC-MS/MS (i.e., the true value of T is higher than when measured in the presence of NaF). The NaF effect was demonstrated not to be related to an impact on the assay itself (LC-MS/MS) but rather an effect on the partitioning of T into the plasma and the cellular components of blood when NaF is added to blood before it is centrifuged. In the presence of NaF, some T partitions into blood cells and this fraction is not available for measurement in plasma.

A second factor to consider when comparing T concentrations in serum and NaF-EDTA plasma measured in men taking oral TU, is the post-collection (i.e., ex vivo) conversion of TU to T by the action of non-specific esterases in blood. This post-collection conversion increases the T measured in the sample compared to the actual T concentration in the subject's circulation. Because the TU to T conversion is an enzymatic reaction mediated by esterases, its rate (extent) is determined by the TU concentration in the blood sample, the temperature of the sample (e.g., RT or on ice), the duration that the sample sits before centrifugation, and the presence of esterase inhibitors in the blood sample (e.g., whether drawing the blood into a tube which contains NaF). This is schematically presented in FIG. 1 which shows that measured T concentrations are different between serum and NaF-EDTA plasma.

The TU concentration in the blood sample depends on the PK profile of the oral TU formulation (and thus is formulation specific) as well as how long after dosing the sample is collected.

The study explored the impact of the variables that determine the slope (M) in FIG. 1, particularly regarding the extent to which they depended on temperature and tube type. TU concentration was not controlled, but the blood samples will be drawn at a proposed dose-titration sample time, and so approximate the clinical setting for titration of oral TU. Based on the analysis, the difference between the T concentration between serum and EDTA-plasma was estimated for particular sample handling conditions. This difference allowed the determination of a correction factor for T concentration for any particular handling situation studied and the T concentration in NaF-EDTA plasma, EDTA plasma, and serum collected in plain tubes.

As shown in FIG. 2, the blue arrows indicate the steps of the conversion for a sample collected 6 hours post-dose in plain tube (allowed to clot at room temperature for 30 minutes) into the expected T concentration if the sample had been collected in a NaF-EDTA tube (and kept on ice for 30 minutes). First, the T concentration in the serum (from the plain tube) is reduced by the factor compensating for TU-to-T conversion at room temperature for 30 minutes (0.959, as indicated by the top arrow). Second, the T concentration is further reduced by the matrix effect associated with NaF-EDTA plasma compared to serum (0.858). Third, the T concentration is increased by the Tu-to-T conversion that occurs when a sample in a NaF-EDTA tube is help on ice for 30 minutes (1.001)

The combined effect (0.959×0.858×1.001=0.824) is the product of the three effects known to affect serum concentration. The expected value of the equivalent T concentration in plasma from a NaF-EDTA tube is 82.4% of the serum value when the incubation temperature, incubation time, and underlying TU concentration are as stated. The reciprocal value (1/0.858=1.214) can be used to convert a NaF-EDTA plasma T concentration into an equivalent serum concentration.

The correction factor allows a T concentration measured in, for example, a plain tube held for 30 minutes at RT to be converted into a corresponding NaF-EDTA plasma concentration which was held for example for 30 minutes on ice. The correction factor is specific for given post-dose time or time-period, since it depends on the TU concentration expected in the blood sample.

Based on the experiment described, to convert a T concentration from a 6 hour (i.e., $C_6$) post-dose sample measured in NaF-EDTA plasma (isolated after blood tube sat on ice for 30 minutes) to the T concentration expected in serum (isolated after blood tube sat at room temperature for 30 minutes), the NaF-EDTA plasma T concentration is multiplied by 1.214. Also, if the sample had been a serum sample, then dividing the T concentration measured in serum by 1.214 would yield the expected T concentration in NaF-EDTA plasma. This 'correction factor' was accounted for in calculating efficacy in the study because the eugonadal range was one which was developed for T levels measured in NaF-EDTA plasma, namely 252-907 ng/dL, and not the 'typical' eugonadal range for serum, namely 300-1000 ng/dL. Thus, when converting the 'typical' eugonadal range for serum collected in plain tubes, the NaF-EDTA plasma range should have the correction factor applied to it, which leads to a 'typical' range of 306-1101 ng/dL. This 'corrected' value can then be used for dose titration decisions.

For the 6 hr sample, going from NaF-EDTA plasma to serum the conversion factor is 1.214 (95% confidence interval: 1.088, 1.340). Going from serum to NaF-EDTA plasma the correction factor is 0.824 (95% confidence interval: 0.743, 0.904).

The conversion factor only has to be about 1.214. In this case about means a difference of less that #15% or 1.032 to 1.396. This degree of difference is the variability allowed in assay validation such as described in the FDA's Bioanalytic Method Validation Guidance for Industry published in May 2018.

Dose Titration

The goal of dose-titration in men treated with oral TU is to bring the testosterone $C_{avg}$ into the eugonadal range. Because titration decisions based on testosterone $C_{avg}$ are not practical in real world clinical setting, single sample T concentrations can be used as surrogates of $C_{avg}$. Concordance analysis estimates how well dose titration based on two different measures (e.g., $C_{avg}$ V. $C_6$) work in guiding dose titration. On-diagonal titration indicates that the two measures result in the same dose-titration decision. However, to determine total concordance, effective off-diagonal titration also must be determined. Effective off-diagonal titration can be estimated for the following reasons. First, testosterone exposure is dose proportional, so it is possible to predict the change in $C_{avg}$ with change in dose. Second, the titration boundaries (425 to 970 ng/dL) fall within the eugonadal boundaries (300 to 1100 ng/dL), and the eugonadal range is wide (3.5 fold) compared to the largest dose increment (33%) or decrement (25%). This means that the dose increments/decrements employed can allow movement within the eugonadal range (e.g. increasing the dose of someone with a $C_{avg}$ of 400 ng/dL will raise the $C_{avg}$ to a maximum of 532 ng/dL [400×1.33]). Similarly, when titration decisions based on $C_6$ are different from those based on $C_{avg}$, the outcome will often be a $C_{avg}$ in the eugonadal range. For example, when a patient's $C_6$ is less than 425 ng/dL (indicating a dose increase is required), but whose $C_{avg}$ is 600 ng/dL (indicating no titration), the impact of titrating based on Co is that the $C_{avg}$ will increase but remain in the eugonadal range. The largest dose increase will result in a 33% increase in exposure which, in this case, will raise the $C_{avg}$ to 798 ng/dL. Therefore, despite titration based on $C_6$, this patient's $C_{avg}$ is not likely to rise above the upper boundary of the eugonadal range. Thus, the titration decision based on $C_6$ is effectively concordant with that based on $C_{avg}$, since both titration decisions will result in a patient with a $C_{avg}$ in the eugonadal range. Selected cells in Table 3 indicate a patient's $C_{avg}$ that would result in effective off-diagonal titration. Therefore, when comparing the effectiveness of dose-titration decisions based on $C_6$ and $C_{avg}$, both concordance (on-diagonal agreement between $C_6$ and $C_{avg}$) and effective off-diagonal agreement must be considered) [i.e., total concordance (percent of patients treated with oral TU who fall into given concordance boxes) is defined as the sum of on-diagonal and effective off-diagonal concordance (see area in Table 3 defined by heavy line). In the example presented, the $C_6$ value is a serum value derived from a measured NaF-EDTA plasma value and a conversion factor that enables the conversion of NaF-EDTA plasma data to be converted to an equivalent serum data.

TABLE 3

| Titration boundaries | | $C_{avg}$ calculated from NaF-EDTA plasma <350 ng/dL | 350 - 800 ng/dl. | >800 ng/dl |
|---|---|---|---|---|
| Serum $C_6$ | < 425 ng/dL Increase dose (maximum 33%) | Concordant | Patients with $C_{avg}$ ≤ 682 ng/dl remain in eugonadal range after dose titration | Discordant |
| | 425 - 970 ng/dl No dose change | Patients with Cary ≥ 252 ng/dl are in eugonadal range | Concordant | Discordant" |

TABLE 3-continued

| | | $C_{avg}$ calculated from NaF-EDTA plasma | | |
|---|---|---|---|---|
| Titration boundaries | | <350 ng/dL | 350 - 800 ng/dl. | >800 ng/dl |
| | > 970 ng/dl. Decrease dose (maximum 25%) | Discordant[a] | All patients remain in eugonadal range despite decrease in dose | Concordant |

Abbreviations:

$C_6$ = concentration 6 hours after morning dose; $C_{avg}$ = average observed concentration over 24 hours Note:

Concordance: when the titration decision based on $C_6$ or $C_{avg}$ was the same. Off-Diagonal Titration Decision: when the titration decision based on $C_6$ results in a dose that will generate a $C_{avg}$ in the cugonadal range.

[a]Although some cases may have effective off-diagonal titrations, these cases are so rare as to not impact the overall concordance.

An analysis of data derived from hypogonadal men treated with oral TU demonstrates that for certain clinic visits, the incidence of appropriate (i.e. concordant) titration decisions approximately 99% (Table 4). These reflect an on-diagonal concordance of 75% and 63% and an effective off-diagonal titration decision of 24% and 36% for Visit 2 and Visit 4b, respectively. Therefore, dose titration based on $C_6$ can effectively adjust a patient's oral TU dose such that his $C_{avg}$ is in the eugonadal range.

TABLE 4

Visit 2 (Concordant + Effective Off-Diagonal Titration = 98.7%)

| | | Cag from NaF-EDTA Plasma | | | |
|---|---|---|---|---|---|
| | Titration boundaries | <350 ng/dL | 350 - 800 ng/dl. | >800 ng/dl | Total |
| $C_6$ derived from NaF-EDTA plasma value | < 425 ng/dl Increase dose (maximum 33 %) | 59.4% | 13.9% (ET = 13.9%) | 0% | 73.3% |
| | 425 - 970 ng/dL No dose change | 5.4% (L'T = 4.2%) | 15.2% | 2% (ET =1.2 %) | 22.6% |
| | > 970 ng/dl. Decrease dose (maximum 25 %) | 0% | 4.2% (ET = 4.2%) | 0.6% | 4.8% |
| | Total | 64.8% | 33.3% | 2.6% | 100% |

Visit 4b (Concordant + Effective Off-Diagonal Titration = 99.1% )

| | | $C_{avg}$ from NaF-EDTA Plasma | | | |
|---|---|---|---|---|---|
| | Titration boundaries | <350 ng/dI. | 350 - 800 ng/dl | >800 ng/dl | Total |
| $C_6$ derived from NaF-EDTA plasma value | <425 ng/dl Increase dose (maximum 33 %) | 37.5% | 21.8% (ET = 21.8%) | 0% | 59.3% |
| | 425 - 970 ng/dl No dose change | 10% (ET = 9.3%) | 25% | 0.6% (ET = 0.6%) | 35.6% |
| | >970 ng/dL Decrease dose (maximum 25%) | 0% | 4.3% (ET = 4.3%) | 0.6% | 4.9% |
| | Total | 47.5% | 51.1% | 1.2% | 100% |

Abbreviations:

$C_6$ = concentration 6 hours after morning dose;

$C_{avg}$ = average observed concentration over 24 hours;

ET = Effective Off-Diagonal Titration Decision

A single sample drawn 6 hours after the AM dose can effectively guide dose titration. The titration decision agreement (concordance plus effectiveness of off-diagonal titration decision) between $C_6$ and $C_{avg}$ was high (about 99%) at the 2 titration visits.

OTHER EMBODIMENTS

The detailed description set-forth above is provided to aid those skilled in the art in practicing the present invention. However, the invention described and claimed herein is not to be limited in scope by the specific embodiments herein disclosed because these embodiments are intended as illustration of several aspects of the invention. Any equivalent embodiments are intended to be within the scope of this invention. Indeed, various modifications of the invention in addition to those shown and described herein will become apparent to those skilled in the art from the foregoing description, which do not depart from the spirit or scope of the present inventive discovery. Such modifications are also intended to fall within the scope of the appended claims.

What is claimed is:

1. A method of treating one or more conditions associated with a deficiency or absence of endogenous testosterone in a population of human male subjects, comprising:

administering a defined dose of testosterone undecanoate to the population in an oral pharmaceutical composition twice daily, once in the morning and once in the evening, wherein the defined dose is about 237 mg of testosterone undecanoate for a total daily dose of about 474 mg of testosterone undecanoate;

measuring serum testosterone concentration in the population at steady state after at least seven days of daily administration of the defined dose and 6 hours after administration of a morning dose; and based on the measured serum testosterone concentration, either:

increasing the defined dose of testosterone undecanoate administered to the subjects in the population to about 316 mg if the measured serum testosterone concentration is less than about 425 ng/dL, maintaining the defined dose of testosterone undecanoate administered to the subjects in the population if the measured serum testosterone concentration is between about 425 ng/dL and about 970 ng/dL; or decreasing the defined dose of testosterone undecanoate administered to the subjects in the population to about 198 mg if the measured serum testosterone concentration in that subject is greater than about 970 ng/dL;

wherein the oral pharmaceutical composition comprises about 18-22% (w/w) testosterone undecanoate solubilized in a carrier comprising about 50% or more oleic acid and about 32% or less hydrophilic surfactant comprising polyoxyethylene (40) hydrogenated castor oil, and wherein the method provides that:

at least about 75% of the population has a $C_{avg}$ in the eugonadal range, and less than about 5% of the population has a $C_{max}$ in the range of about 1800 ng/dL to about 2500 ng/dL.

2. The method of claim 1, wherein the measuring is performed from serum collected in a plain tube.

3. The method of claim 1, wherein the one or more conditions are selected from primary hypogonadism and hypogonadotropic hypogonadism.

4. The method of claim 3, wherein the one or more conditions is hypogonadotropic hypogonadism caused by gonadotropin or luteinizing hormone-releasing hormone (LHRH) deficiency or pituitary-hypothalamic injury from tumors, trauma, or radiation.

5. The method of claim 1, wherein if the defined dose of testosterone undecanoate is increased to about 316 mg for a total daily dose of about 632 mg of testosterone undecanoate the method further comprises:

remeasuring the serum testosterone concentration in the subjects in the population who received an increased dose at steady state after at least seven days of daily administration of the increased defined dose of about 316 mg and 6 hours after administration of a morning dose; and based on the remeasured serum testosterone concentration, either:

increasing the defined dose of testosterone undecanoate administered to the subjects in the population who received the increased dose to about 396 mg if the serum testosterone concentration is less than about 425 ng/dL;

maintaining the defined dose of testosterone undecanoate administered to the subjects in the population who received the increased dose if the measured serum testosterone concentration is between about 425 ng/dL and about 970 ng/dL; or decreasing the defined dose of testosterone undecanoate administered to the subjects in the population who received the increased dose to about 237 mg if the serum testosterone concentration is greater than about 970 ng/dL.

6. The method of claim 1, wherein if the defined dose of testosterone undecanoate is decreased to about 198 mg for a total daily dose of about 396 mg of testosterone undecanoate the method further comprises:

remeasuring the serum testosterone concentration in subjects in the population who received a decreased dose at steady state after at least seven days of daily administration of the decreased defined dose of about 198 mg and 6 hours after administration of a morning dose; and based on the remeasured serum testosterone concentration, either:

increasing the defined dose of testosterone undecanoate administered to the subjects in the population who received the decreased dose to about 237 mg if the serum testosterone concentration is less than about 425 ng/dL;

maintaining the defined dose of testosterone undecanoate administered to the subjects in the population who received the decreased dose if the measured serum testosterone concentration is between about 425 ng/dL and about 970 ng/dL; or decreasing the defined dose of testosterone undecanoate administered to the subjects in the population who received the decreased dose to about 158 mg if the serum testosterone concentration is greater than about 970 ng/dL.

7. The method of claim 1, wherein the oral pharmaceutical composition comprises a digestible oil.

8. The method of claim 1, wherein the oral pharmaceutical composition further comprises borage seed oil and peppermint oil.

9. The method of claim 1, wherein the oral pharmaceutical composition comprises about 50-70% (w/w) oleic acid and about 5-20% (w/w) polyoxyethylene (40) hydrogenated castor oil.

10. The method of claim 9, wherein the oral pharmaceutical composition comprises about 50-70% (w/w) oleic acid, about 5-20% (w/w) polyoxyethylene (40) hydrogenated castor oil and about 10-15% (w/w) digestible oil.

11. The method of claim 1, wherein the defined dose administered to the population is decreased to no less than about 158 mg twice daily and increased to no more than about 396 mg twice daily for a total daily dose of testosterone undecanoate of from about 316 mg to about 792 mg, wherein a single increase of the defined dose is not more than 33%, and wherein a single decrease of the defined dose is not more than 25%.

12. The method of claim 1, wherein greater than or equal to about 85% of the population has a $C_{max}$ below about 1500 ng/dL.

13. The method of claim 5, wherein the defined dose administered to the population is decreased to no less than about 158 mg twice daily and increased to no more than about 396 mg twice daily for a total daily dose of testosterone undecanoate of from about 316 mg to about 792 mg, wherein a single increase of the defined dose is not more than 33%, and wherein a single decrease of the defined dose is not more than 25%.

14. The method of claim 6, wherein the defined dose administered to the population is decreased to no less than about 158 mg twice daily and increased to no more than about 396 mg twice daily for a total daily dose of testosterone undecanoate of from about 316 mg to about 792 mg, wherein a single increase of the defined dose is not more than 33%, and wherein a single decrease of the defined dose is not more than 25%.

15. A method of treating one or more conditions associated with a deficiency or absence of endogenous testosterone in a population of human male subjects, comprising:

administering a defined dose of testosterone undecanoate to the population in an oral pharmaceutical composition twice daily, once in the morning and once in the evening for a time period of at least seven days, wherein the defined dose is about 237 mg of testosterone undecanoate for a total daily dose of about 474 mg of testosterone undecanoate;

measuring serum testosterone concentration in the population at steady state after at least seven days of daily administration of the defined dose and 6 hours after administration of a morning dose; and based on the measured serum testosterone concentration, either:

increasing the defined dose of testosterone undecanoate administered to subjects in the population by about 33% if the measured serum testosterone concentration is less than about 425 ng/dL, maintaining the defined dose of testosterone undecanoate administered to subjects in the population if the measured serum testosterone concentration is between about 425 ng/dL and about 970 ng/dL; or decreasing the defined dose of testosterone undecanoate administered to subjects in the population by about 16% if the measured serum testosterone concentration is greater than about 970 ng/dL;

wherein the oral pharmaceutical composition comprises about 18-22% (w/w) testosterone undecanoate solubilized in a carrier comprising about 50% or more oleic acid and about 32% or less hydrophilic surfactant comprising polyoxyethylene (40) hydrogenated castor oil, and wherein the method provides that:

at least about 75% of the population has a $C_{avg}$ in the eugonadal range, and less than about 5% of the population has a $C_{max}$ in the range of about 1800 ng/dL to about 2500 ng/dL.

16. The method of claim 15, wherein the one or more conditions are selected from primary hypogonadism and hypogonadotropic hypogonadism.

17. The method of claim 15, wherein the oral pharmaceutical composition comprises about 50-70% (w/w) oleic acid, about 5-20% (w/w) polyoxyethylene (40) hydrogenated castor oil, and about 10-15% (w/w) digestible oil comprising borage seed oil and peppermint oil.

18. The method of claim 15, wherein the defined dose administered to the population is decreased to no less than about 158 mg twice daily and increased to no more than about 396 mg twice daily for a total daily dose of testosterone undecanoate of from about 316 mg to about 792 mg, wherein a single increase of the defined dose is not more than 33%, and wherein a single decrease of the defined dose is not more than 25%.

19. The method of claim 15, wherein greater than or equal to about 85% of the population has a $C_{max}$ below about 1500 ng/dL.

20. A method of treating one or more conditions associated with a deficiency or absence of endogenous testosterone in a population of human male subjects, comprising:

administering a defined dose of testosterone undecanoate to the population in an oral pharmaceutical composition twice daily, once in the morning and once in the evening for a time period of at least seven days, wherein the defined dose is about 237 mg of testosterone undecanoate for a total daily dose of about 474 mg of testosterone undecanoate;

measuring serum testosterone concentration in the population at steady state after at least seven days of daily administration of the defined dose and 6 hours after administration of a morning dose; and based on the measured serum testosterone concentration, adjusting the defined dose administered to subjects in the population to no less than about 158 mg twice daily and no more than about 396 mg twice daily for a total daily dose of testosterone undecanoate of from about 316 mg to about 792 mg, thereby maintaining the measured serum testosterone concentration in the subjects between about 425 ng/dL and about 970 ng/dL, wherein a single increase of the defined dose is not more than 33%, wherein a single decrease of the defined dose is not more than 25%, wherein the oral pharmaceutical composition comprises about 18-22% (w/w) testosterone undecanoate solubilized in a carrier comprising about 50% or more oleic acid and about 32% or less hydrophilic surfactant comprising polyoxyethylene (40) hydrogenated castor oil, and wherein the method provides that:

at least about 75% of the population has a $C_{avg}$ in the eugonadal range, and less than 5% of the population has a $C_{max}$ in the range of about 1800 ng/dL to about 2500 ng/dL.

21. The method of claim 20, wherein the one or more conditions are selected from primary hypogonadism and hypogonadotropic hypogonadism.

22. The method of claim 20, wherein the oral pharmaceutical composition comprises about 50-70% (w/w) oleic acid, about 5-20% (w/w) polyoxyethylene (40) hydrogenated castor oil, and about 10-15% (w/w) digestible oil comprising borage seed oil and peppermint oil.

23. The method of claim 20, wherein greater than or equal to about 85% of the population has a $C_{max}$ below about 1500 ng/dL.

* * * * *